US012780888B2

(12) United States Patent
Gompels

(10) Patent No.: US 12,780,888 B2

(45) Date of Patent: Nov. 3, 2026

(54) IMMUNOMODULATOR

(71) Applicant: Virothera Ltd, Cambridge (GB)

(72) Inventor: Ursula Gompels, London (GB)

(73) Assignee: Virothera Limited, Cambridge (GB)

( * ) Notice: Subject to any disclaimer, the term of this patent is extended or adjusted under 35 U.S.C. 154(b) by 860 days.

(21) Appl. No.: 17/916,093

(22) PCT Filed: Apr. 1, 2021

(86) PCT No.: PCT/EP2021/058776
§ 371 (c)(1),
(2) Date: Sep. 30, 2022

(87) PCT Pub. No.: WO2021/198500
PCT Pub. Date: Oct. 7, 2021

(65) Prior Publication Data

US 2023/0141043 A1 May 11, 2023

(30) Foreign Application Priority Data

Apr. 3, 2020 (GB) ...................................... 2004977

(51) Int. Cl.

| | |
|---|---|
| ***C07H 21/00*** | (2006.01) |
| ***A61K 39/245*** | (2006.01) |
| ***A61K 39/39*** | (2006.01) |
| ***A61P 31/22*** | (2006.01) |
| ***C07K 14/52*** | (2006.01) |
| ***C12Q 1/6883*** | (2018.01) |
| *A61K 38/00* | (2006.01) |
| *A61K 39/00* | (2006.01) |

(52) U.S. Cl.
CPC .......... *C07K 14/523* (2013.01); *A61K 39/245* (2013.01); *A61K 39/39* (2013.01); *A61P 31/22* (2018.01); *C12Q 1/6883* (2013.01); *A61K 38/00* (2013.01); *A61K 2039/55522* (2013.01); *C12Q 2600/156* (2013.01)

(58) Field of Classification Search
None
See application file for complete search history.

(56) References Cited

FOREIGN PATENT DOCUMENTS

| | | | |
|---|---|---|---|
| CN | 116635087 | A | 8/2023 |
| CN | 118556073 | A | 8/2024 |
| WO | 2006/126025 | A2 | 11/2006 |
| WO | 2012/109314 | A2 | 8/2012 |

OTHER PUBLICATIONS

Catusse et al., CCR5 signalling, but not DARC or D6 regulatory, chemokine receptors are targeted by herpesvirus U83A chemokine which delays receptor internalisation via diversion to a caveolin-linked pathway. J Inflamm (Lond). Jul. 30, 2009;6:22, 12 pages.

Catusse et al., Inhibition of HIV-1 infection by viral chemokine U83A via high-affinity CCR5 interactions that block human chemokine-induced leukocyte chemotaxis and receptor internalization. Blood. May 1, 2007;109(9):3633-9.

GenBank Accession No. MK630134, Human betaherpesvirus 6A strain MOW-F1M, partial genome. 117 pages, May 12, 2019.

Geneseq Accession No. AEM36517, Human herpesvirus 6A U83AN-pep short splice variant protein. 1 page, Feb. 22, 2007.

Geneseq Accession No. AEM36521, Human herpesvirus 6A U83AN-pep short splice variant protein. 1 page, Feb. 22, 2007.

Peddu et al., Inherited Chromosomally Integrated Human Herpesvirus 6 Demonstrates Tissue-Specific RNA Expression In Vivo That Correlates with an Increased Antibody Immune Response. J Virol. Dec. 12, 2019;94(1): e01418-19, 14 pages.

Pontejo et al., Chemokine Subversion by Human Herpesviruses. J Innate Immun. 2018; 10(5-6):465-478.

UniProtKB Accession No. A0A5P9VIK2, Full-Chemokine. 1 pages, Feb. 26, 2020.

International Search Report and Written Opinion for Application No. PCT/EP2021/058776, dated Aug. 4, 2021, 15 pages.

Dewin et al., Identification and characterization of U83A viral chemokine, a broad and potent beta-chemokine agonist for human CCRs with unique selectivity and inhibition by spliced isoform. J Immunol. Jan. 1, 2006;176(1):544-56.

GenBank Accession No. AIX09949, chemokine U83A (endogenous virus) [*Homo sapiens*]. 1 page, Feb. 5, 2015.

Gompels et al., Immunisation Using Novel DNA Vaccine Encoding Virus Membrane Fusion Complex and Chemokine Genes Shows High Protection from HSV-2. Viruses. Oct. 22, 2022; 14(11):2317, 18 pages.

Sin et al., DNA vaccines encoding interleukin-8 and Rantes enhance antigen-specific Th1-type CD4(+) T-cell-mediated protective immunity against herpes simplex virus type 2 in vivo. J Virol. Dec. 2000; 74(23):11173-80.

Tweedy et al., Analyses of germline, chromosomally integrated human herpesvirus 6A and B genomes indicate emergent infection and new inflammatory mediators. J Gen Virol. Feb. 2015;96(Pt 2):370-389.

GenBank Accession No. QBQ65302, U83 [Human betaherpesvirus 6A]. 1 page, Apr. 2, 2019.

GenBank Accession No. QFX63816, hypothetical protein [Human betaherpesvirus6]. 1 page, Oct. 31, 2019.

GenBank Accesson No. AB443462, Human herpesvirus 6A U83 gene for chemokine, complete cds, strain: U1102, clone: Feb. 1, 43. 1 page, Feb. 26, 2009.

*Primary Examiner* — Michail A Belyavskyi

(74) *Attorney, Agent, or Firm* — McCarter & English, LLP; Yu Lu; Thao H. Nguyen

(57) ABSTRACT

The present invention relates to an immunomodulator, and in particular to a chemokine-5 like agent with activities with a range of chemokine receptors. The invention relates to the use of this chemokine-like agent and variants thereof as a medicament.

19 Claims, 11 Drawing Sheets

Specification includes a Sequence Listing.

FIGURE 1

Integrated iciU83A from iciHHV-6A (KP128710.1)integrated at 17p13.3; features noted

```
atg tcc att cgg ctt ttt att gg(t ttt ttt t)at acg gca tat att ggt atg gct atc gga primer pairs (polyT)
 M   S   I   R   L   F   I   G   F   F   Y   T   A   Y   I   G   M   A   I   G
ttt ata tgt agt tcc ccc gat gcg gag ctg ttt tcc gaa aaa tca cgt att tcg tct tct SNP g-t/M-I no int init
 F   I   C   S   S   P   D   A   E   L   F   S   E   K   S   R   I   S   S   S  to mutate spl don cct-cca
gtc ttg tta gga tgt ttg ttg tgt tgc atg gat tgg tcc gct gcc gta c(ct ggg aaa aca to mutate DR gta-gtg
 V   L   L   G   C   L   L   C   C   M   D   W   S   A   A   V   P   G   K   T   probe primer
gag cct ttt aga aaa ctt ttt gat gca atc atg att aaa aag cta aaa agt tgt tct gct  (intron) encodes GAG binding
 E   P   F   R   K   L   F   D   A   I   M   I   K   K   L   K   S   C   S   A   to mutate ccg-cca pro
gct tac) ccg tct ggt ttg gag cag ggc tcg atg tgt gat atg gca gat gca tcg ccg aca to mutate spl ac tac-tat tyr
 A   Y   P   S   G   L   E   Q   G   S   M   C   D   M   A   D   A   S   P   T   SNP a-g/D-G in splice stop
agt ctt gaa tta gga ttg tcg aaa tta gac aaa gaa tca tga
 S   L   E   L   G   L   S   K   L   D   K   E   S   -
```

FIGURE 2

Spliced integrated iciU83A-N from iciHHV-6A with features noted

```
atg tcc att cgg ctt ttt att ggt ttt ttt tat acg gca tat att ggt atg gct atc gga
 M   S   I   R   L   F   I   G   F   F   Y   T   A   Y   I   G   M   A   I   G
ttt ata tgt agt tcc ccc gat gcg gag ctg ttt tcc gaa aaa tca cgt att tcg tct tct
 F   I   C   S   S   P   D   A   E   L   F   S   E   K   S   R   I   S   S   S  DR- TACC spliced
gtc ttg tta gga tgt ttg ttg tgt tgc atg gat tgg tcc gct gcc gta ccc gtc tgg ttt splice f/s
 V   L   L   G   C   L   L   C   C   M   D   W   S   A   A   V   P   V   W   F  SNP tga-tgg/*-W
gga gca ggg ctc gat gtg tga tat ggc aga tgc atc gcc gac aag tct tga att agg att gains 8aa to
 G   A   G   L   D   V   *                                                      next stop tga
gtc gaa att aga caa aga atc atg a
```

Gene without proximal splice site SNP showing splice to stop codon:

```
...gta ccc gtc tga ttt ...
... V   P   V   *      ...
```

FIGURE 3

A

Integrated iciHHV-6A iciU83A diagnostic primer pair and probe or primer pair atg tcc att cgg ctt ttt att ggt ttt ttt tat acg gca tat att ggt atg gct atc gga
M S I R L F I G F F Y T A Y I G M A I G
ttt ata tgt agt tcc ccc gat gcg gag ctg ttt tcc gaa aaa tca cgt att tcg tct tct
F I C S S P D A E L F S E K S R I S S S
gtc ttg tta gga tgt ttg ttg tgt tgc atg gat tgg tcc gct gcc gta c(ct ggg aaa aca (intron)
V L L G C L L C C M D W S A A V P G K T
gag cct ttt aga aaa ctt ttt gat gca atc atg att aaa aag cta aaa agt tgt tct gct probe
E P F R K L F D A I M I K K L K S C S A
gct tac) ccg tct ggt ttg gag cag ggc tcg atg tgt gat atg gca gat gca tcg ccg aca 3'end SNP
A Y P S G L E Q G S M C D M A D A S P T
agt ctt gaa tta gga ttg tcg aaa tta gac aaa gaa tca tga
S L E L G L S K L D K E S -

B

Spliced iciHHV-6A iciU83A diagnostic primer pair and probe or nested primer atg tcc att cgg ctt ttt att ggt ttt ttt tat acg gca tat att ggt atg gct atc gga
M S I R L F I G F F Y T A Y I G M A I G
ttt ata tgt agt tcc ccc gat gcg gag ctg ttt tcc gaa aaa tca cgt att tcg tct tct
F I C S S P D A E L F S E K S R I S S S DR spliced
gtc ttg tta gga tgt ttg ttg tgt tgc atg gat tgg tcc gct gcc gta ccc gtc tgg ttt splice f/s
V L L G C L L C C M D W S A A V P V W F SNP tga-tgg
gga gca ggg ctc gat gtg tga tat ggc aga tgc atc gcc gac aag tct tga att agg att gain 8aa to
G A G L D V * next stop
gtc gaa att aga caa aga atc atg a

SEQUENCE LISTING

```
<160> NUMBER OF SEQ ID NOS: 24

<210> SEQ ID NO 1
<211> LENGTH: 207
<212> TYPE: DNA
<213> ORGANISM: Human herpesvirus 6A

<400> SEQUENCE: 1

gtcgaaatgt ccattcggct ttttattggt ttttttata cggcatatat tggtatggct      60
```

atcggattta tatgtagttc ccccgatgcg gagctgtttt ccgaaaaatc acgtatttcg 120
tcttctgtct tgttaggatg tttgttgtgt tgcatggatt ggtccgctgc cgtacccgtc 180
tggtttggag cagggctcga tgtgtga 207

<210> SEQ ID NO 2
<211> LENGTH: 207
<212> TYPE: DNA
<213> ORGANISM: Human herpesvirus 6A

<400> SEQUENCE: 2
gtcgaaatgt ccattcggct ttttattggt ttcttttata cggcatatat tggtatggct 60
atcggattta tatgtagttc ccccgatgcg gagctgtttt ccgaaaaatc acgtatttcg 120
tcttctgtct tgttaggatg tttgttgtgt tgcatggatt ggtccgctgc cgtacccgtc 180
tggtttggag cagggctcga tgtgtga 207

<210> SEQ ID NO 3
<211> LENGTH: 207
<212> TYPE: DNA
<213> ORGANISM: Human herpesvirus 6A

<400> SEQUENCE: 3
gtcgaaatgt ccatccgcct tttcattggc ttcttttaca cagcatacat cgggatggct 60
ataggcttca tttgctcctc tccagacgcg gagctgtttt cagagaaaag ccggatatct 120
agtagcgtgc tgctcggatg tctgctctgt tgcatggact ggtccgctgc cgtcccagtg 180
tggttcggcg ctggactgga tgtgtga 207

<210> SEQ ID NO 4
<211> LENGTH: 66
<212> TYPE: PRT
<213> ORGANISM: Human herpesvirus 6A

<400> SEQUENCE: 4

Met Ser Ile Arg Leu Phe Ile Gly Phe Phe Tyr Thr Ala Tyr Ile Gly
1               5                   10                  15

Met Ala Ile Gly Phe Ile Cys Ser Ser Pro Asp Ala Glu Leu Phe Ser
            20                  25                  30

Glu Lys Ser Arg Ile Ser Ser Ser Val Leu Leu Gly Cys Leu Leu Cys
        35                  40                  45

Cys Met Asp Trp Ser Ala Ala Val Pro Val Trp Phe Gly Ala Gly Leu
    50                  55                  60

Asp Val
65

<210> SEQ ID NO 5
<211> LENGTH: 46
<212> TYPE: PRT
<213> ORGANISM: Human herpesvirus 6A

<400> SEQUENCE: 5

Phe Ile Cys Ser Ser Pro Asp Ala Glu Leu Phe Ser Glu Lys Ser Arg
1               5                   10                  15

Ile Ser Ser Ser Val Leu Leu Gly Cys Leu Leu Cys Cys Met Asp Trp
            20                  25                  30

Ser Ala Ala Val Pro Val Trp Phe Gly Ala Gly Leu Asp Val
        35                  40                  45

<210> SEQ ID NO 6
<211> LENGTH: 348
<212> TYPE: DNA
<213> ORGANISM: Human herpesvirus 6A

<400> SEQUENCE: 6

```
gtcgaaatgt ccattcggct ttttattggt ttcttttata cggcatatat tggtatggct     60

atcggattta tatgtagttc ccccgatgcg gagctgtttt ccgaaaaatc acgtatttcg    120

tcttctgtct tgttaggatg tttgttgtgt tgcatggatt ggtccgctgc cgtacctggg    180

aaaacagagc cttttagaaa actttttgat gcaatcatga ttaaaaagct aaaaagttgt    240

tctgctgctt acccgtctgg tttggagcag ggctcgatgt gtgatatggc agatgcatcg    300

ccgacaagtc ttgaattagg attgtcgaaa ttagacaaag aatcatga                348
```

<210> SEQ ID NO 7
<211> LENGTH: 348
<212> TYPE: DNA
<213> ORGANISM: Human herpesvirus 6A

<400> SEQUENCE: 7

```
gtcgaaatgt ccattcggct ttttattggt ttttttttata cggcatatat tggtatggct     60

atcggattta tatgtagttc ccccgatgcg gagctgtttt ccgaaaaatc acgtatttcg    120

tcttctgtct tgttaggatg tttgttgtgt tgcatggatt ggtccgctgc cgtgccaggg    180

aaaacagagc cttttagaaa actttttgat gcaatcatga ttaaaaagct aaaaagttgt    240

tctgctgctt atccatctgg tttggagcag ggctcgatgt gtgatatggc agatgcatcg    300

ccgacaagtc ttgaattagg attgtcgaaa ttagacaaag aatcatga                348
```

<210> SEQ ID NO 8
<211> LENGTH: 348
<212> TYPE: DNA
<213> ORGANISM: Human herpesvirus 6A

<400> SEQUENCE: 8

```
gtcgaaatgt ccattcggct ttttattggt ttcttttata cggcatatat tggtatggct     60

atcggattta tatgtagttc ccccgatgcg gagctgtttt ccgaaaaatc acgtatttcg    120

tcttctgtct tgttaggatg tttgttgtgt tgcatggatt ggtccgctgc cgtgccaggg    180

aaaacagagc cttttagaaa actttttgat gcaatcatga ttaaaaagct aaaaagttgt    240

tctgctgctt atccatctgg tttggagcag ggctcgatgt gtgatatggc agatgcatcg    300

ccgacaagtc ttgaattagg attgtcgaaa ttagacaaag aatcatga                348
```

<210> SEQ ID NO 9
<211> LENGTH: 348
<212> TYPE: DNA
<213> ORGANISM: Human herpesvirus 6A

<400> SEQUENCE: 9

```
gtcgaaatga gcatcagact gttcatcggc ttcttctaca ccgcctacat cggcatggcc     60

atcggcttca tctgcagcag ccccgacgcc gagctgttca gcgagaagag cagaatcagc    120

agcagcgtgc tgctgggctg cctgctgtgc tgcatggact ggagcgccgc cgtgccaggc    180

aagaccgagc ccttcagaaa gctgttcgac gccatcatga tcaagaagct gaagagctgc    240

agcgccgcct atcctagcgg cctggagcag ggcagcatgt gcgacatggc cgacgccagc    300

cccaccagcc tggagctggg cctgagcaag ctggacaagg agagctga                348
```

<210> SEQ ID NO 10
<211> LENGTH: 22
<212> TYPE: DNA
<213> ORGANISM: Artificial Sequence
<220> FEATURE:
<223> OTHER INFORMATION: Synthetic - primer

<400> SEQUENCE: 10
atgtccattc ggctttttat tg 22

<210> SEQ ID NO 11
<211> LENGTH: 22
<212> TYPE: DNA
<213> ORGANISM: Artificial Sequence
<220> FEATURE:
<223> OTHER INFORMATION: Synthetic - primer

<400> SEQUENCE: 11
tcatgattct ttgtctaatt tc 22

<210> SEQ ID NO 12
<211> LENGTH: 38
<212> TYPE: DNA
<213> ORGANISM: Artificial Sequence
<220> FEATURE:
<223> OTHER INFORMATION: Synthetic - probe/primer

<400> SEQUENCE: 12
aaaaagctaa aaagttgttc tgctgcttac ccgtctgg 38

<210> SEQ ID NO 13
<211> LENGTH: 24
<212> TYPE: DNA
<213> ORGANISM: Artificial Sequence
<220> FEATURE:
<223> OTHER INFORMATION: Synthetic - probe/primer

<400> SEQUENCE: 13
tggtccgctg ccgtacccgt ctgg 24

<210> SEQ ID NO 14
<211> LENGTH: 113
<212> TYPE: PRT
<213> ORGANISM: Human herpesvirus 6A

<400> SEQUENCE: 14

```
Met Ser Ile Arg Leu Phe Ile Gly Phe Phe Tyr Thr Ala Tyr Ile Gly
1               5                   10                  15

Met Ala Ile Gly Phe Ile Cys Ser Ser Pro Asp Ala Glu Leu Phe Ser
            20                  25                  30

Glu Lys Ser Arg Ile Ser Ser Ser Val Leu Leu Gly Cys Leu Leu Cys
        35                  40                  45

Cys Met Asp Trp Ser Ala Ala Val Pro Gly Lys Thr Glu Pro Phe Arg
    50                  55                  60

Lys Leu Phe Asp Ala Ile Met Ile Lys Lys Leu Lys Ser Cys Ser Ala
65                  70                  75                  80

Ala Tyr Pro Ser Gly Leu Glu Gln Gly Ser Met Cys Asp Met Ala Asp
                85                  90                  95

Ala Ser Pro Thr Ser Leu Glu Leu Gly Leu Ser Lys Leu Asp Lys Glu
            100                 105                 110

Ser
```

<210> SEQ ID NO 15
<211> LENGTH: 93
<212> TYPE: PRT
<213> ORGANISM: Human herpesvirus 6A

<400> SEQUENCE: 15

```
Phe Ile Cys Ser Ser Pro Asp Ala Glu Leu Phe Ser Glu Lys Ser Arg
1               5                   10                  15

Ile Ser Ser Ser Val Leu Leu Gly Cys Leu Leu Cys Cys Met Asp Trp
            20                  25                  30

Ser Ala Ala Val Pro Gly Lys Thr Glu Pro Phe Arg Lys Leu Phe Asp
        35                  40                  45

Ala Ile Met Ile Lys Lys Leu Lys Ser Cys Ser Ala Ala Tyr Pro Ser
    50                  55                  60

Gly Leu Glu Gln Gly Ser Met Cys Asp Met Ala Asp Ala Ser Pro Thr
65                  70                  75                  80

Ser Leu Glu Leu Gly Leu Ser Lys Leu Asp Lys Glu Ser
                85                  90
```

<210> SEQ ID NO 16
<211> LENGTH: 342
<212> TYPE: DNA
<213> ORGANISM: Human herpesvirus 6A

<400> SEQUENCE: 16

```
atgtccattc ggctttttat tggttttttt tatacggcat atattggtat ggctatcgga     60

tttatatgta gttcccccga tgcggagctg ttttccgaaa aatcacgtat ttcgtcttct    120

gtcttgttag gatgtttgtt gtgttgcatg gattggtccg ctgccgtacc tgggaaaaca    180

gagcctttta gaaaactttt tgatgcaatc atgattaaaa agctaaaaag ttgttctgct    240

gcttacccgt ctggtttgga gcagggctcg atgtgtgata tggcagatgc atcgccgaca    300

agtcttgaat taggattgtc gaaattagac aaagaatcat ga                       342
```

<210> SEQ ID NO 17
<211> LENGTH: 113
<212> TYPE: PRT
<213> ORGANISM: Human herpesvirus 6A

<400> SEQUENCE: 17

```
Met Ser Ile Arg Leu Phe Ile Gly Phe Phe Tyr Thr Ala Tyr Ile Gly
1               5                   10                  15

Met Ala Ile Gly Phe Ile Cys Ser Ser Pro Asp Ala Glu Leu Phe Ser
            20                  25                  30

Glu Lys Ser Arg Ile Ser Ser Ser Val Leu Leu Gly Cys Leu Leu Cys
        35                  40                  45

Cys Met Asp Trp Ser Ala Ala Val Pro Gly Lys Thr Glu Pro Phe Arg
    50                  55                  60

Lys Leu Phe Asp Ala Ile Met Ile Lys Lys Leu Lys Ser Cys Ser Ala
65                  70                  75                  80

Ala Tyr Pro Ser Gly Leu Glu Gln Gly Ser Met Cys Asp Met Ala Asp
                85                  90                  95

Ala Ser Pro Thr Ser Leu Glu Leu Gly Leu Ser Lys Leu Asp Lys Glu
            100                 105                 110

Ser
```

<210> SEQ ID NO 18

<211> LENGTH: 265
<212> TYPE: DNA
<213> ORGANISM: Human herpesvirus 6A

<400> SEQUENCE: 18
atgtccattc ggctttttat tggttttttt tatacggcat atattggtat ggctatcgga 60
tttatatgta gttcccccga tgcggagctg ttttccgaaa aatcacgtat ttcgtcttct 120
gtcttgttag gatgtttgtt gtgttgcatg gattggtccg ctgccgtacc cgtctggttt 180
ggagcagggc tcgatgtgtg atatggcaga tgcatcgccg acaagtcttg aattaggatt 240
gtcgaaatta gacaaagaat catga 265

<210> SEQ ID NO 19
<211> LENGTH: 66
<212> TYPE: PRT
<213> ORGANISM: Human herpesvirus 6A

<400> SEQUENCE: 19

Met Ser Ile Arg Leu Phe Ile Gly Phe Phe Tyr Thr Ala Tyr Ile Gly
1 5 10 15

Met Ala Ile Gly Phe Ile Cys Ser Ser Pro Asp Ala Glu Leu Phe Ser
20 25 30

Glu Lys Ser Arg Ile Ser Ser Ser Val Leu Leu Gly Cys Leu Leu Cys
35 40 45

Cys Met Asp Trp Ser Ala Ala Val Pro Val Trp Phe Gly Ala Gly Leu
50 55 60

Asp Val
65

<210> SEQ ID NO 20
<211> LENGTH: 15
<212> TYPE: DNA
<213> ORGANISM: Human herpesvirus 6A

<400> SEQUENCE: 20
gtacccgtct gattt 15

<210> SEQ ID NO 21
<211> LENGTH: 342
<212> TYPE: DNA
<213> ORGANISM: Human herpesvirus 6A

<400> SEQUENCE: 21
atgtccattc ggctttttat tggttttttt tatacggcat atattggtat ggctatcgga 60
tttatatgta gttcccccga tgcggagctg ttttccgaaa aatcacgtat ttcgtcttct 120
gtcttgttag gatgtttgtt gtgttgcatg gattggtccg ctgccgtacc tgggaaaaca 180
gagcctttta gaaaactttt tgatgcaatc atgattaaaa agctaaaaag ttgttctgct 240
gcttacccgt ctggtttgga gcagggctcg atgtgtgata tggcagatgc atcgccgaca 300
agtcttgaat taggattgtc gaaattagac aaagaatcat ga 342

<210> SEQ ID NO 22
<211> LENGTH: 113
<212> TYPE: PRT
<213> ORGANISM: Human herpesvirus 6A

<400> SEQUENCE: 22

Met Ser Ile Arg Leu Phe Ile Gly Phe Phe Tyr Thr Ala Tyr Ile Gly
1 5 10 15

-continued

```
Met Ala Ile Gly Phe Ile Cys Ser Ser Pro Asp Ala Glu Leu Phe Ser
            20                  25                  30

Glu Lys Ser Arg Ile Ser Ser Ser Val Leu Leu Gly Cys Leu Leu Cys
        35                  40                  45

Cys Met Asp Trp Ser Ala Ala Val Pro Gly Lys Thr Glu Pro Phe Arg
    50                  55                  60

Lys Leu Phe Asp Ala Ile Met Ile Lys Lys Leu Lys Ser Cys Ser Ala
65                  70                  75                  80

Ala Tyr Pro Ser Gly Leu Glu Gln Gly Ser Met Cys Asp Met Ala Asp
                85                  90                  95

Ala Ser Pro Thr Ser Leu Glu Leu Gly Leu Ser Lys Leu Asp Lys Glu
            100                 105                 110

Ser


<210> SEQ ID NO 23
<211> LENGTH: 265
<212> TYPE: DNA
<213> ORGANISM: Human herpesvirus 6A

<400> SEQUENCE: 23

atgtccattc ggctttttat tggtttttt tatacggcat atattggtat ggctatcgga      60

tttatatgta gttcccccga tgcggagctg ttttccgaaa aatcacgtat ttcgtcttct    120

gtcttgttag gatgtttgtt gtgttgcatg gattggtccg ctgccgtacc cgtctggttt    180

ggagcagggc tcgatgtgtg atatggcaga tgcatcgccg acaagtcttg aattaggatt    240

gtcgaaatta gacaaagaat catga                                          265


<210> SEQ ID NO 24
<211> LENGTH: 66
<212> TYPE: PRT
<213> ORGANISM: Human herpesvirus 6A

<400> SEQUENCE: 24

Met Ser Ile Arg Leu Phe Ile Gly Phe Phe Tyr Thr Ala Tyr Ile Gly
1               5                   10                  15

Met Ala Ile Gly Phe Ile Cys Ser Ser Pro Asp Ala Glu Leu Phe Ser
            20                  25                  30

Glu Lys Ser Arg Ile Ser Ser Ser Val Leu Leu Gly Cys Leu Leu Cys
        35                  40                  45

Cys Met Asp Trp Ser Ala Ala Val Pro Val Trp Phe Gly Ala Gly Leu
    50                  55                  60

Asp Val
65
```

IMMUNOMODULATOR

CROSS REFERENCE TO RELATED APPLICATIONS

This application is a U.S. National Stage Application filed under 35 U.S.C. § 371, based on International Patent Application No. PCT/EP2021/058776, filed on Apr. 1, 2021, which claims priority to GB Patent Application No. 2004977.1, filed on Apr. 3, 2020. The entire contents of each of the above applications, including any sequence listing, are incorporated herein by reference.

FIELD OF THE INVENTION

The present invention relates to an immunomodulator, and in particular to a chemokine-like agent with activities with a range of chemokine receptors. The invention relates to the use of this chemokine-like agent and variants thereof as a medicament.

BACKGROUND OF THE INVENTION

Immunotherapy using advanced therapy strategies holds much promise for the treatment of wide areas of pathology, including infectious disease, cancer and autoimmunity. Advanced therapies are classed as combinations of gene delivery, which can be used in different ways, from purposes such as gene therapy to gene delivery together with an immunomodulator, also termed DNA immunotherapy. Early concerns in the applications of gene delivery in vivo centred around perceived hazards from potential DNA integration into the host genome, with consequent gene disruption and dysregulation that could, for example, lead to development of cancer. However, in over 20 years of testing and over 30,000 doses in humans in various trials, gene delivery by DNA vaccination has had an outstanding safety record, and there has been little evidence for either DNA integration or maintenance of residual DNA. There are now known cellular mechanisms, which regulate free DNA within the cell (for example the cGAS pathway) and therefore ad hoc introduction of DNA into the genome is rare. This has led to re-evaluation by the Regulatory committees evaluating DNA vaccines and advanced therapies, including at a recent World Health Organisation consulting committee on nucleic acid vaccines (2018/19), with recommendations in preparation. The object is to streamline and fast-track development of DNA vaccine approaches, this is critical for engaging rapid development for medical emergencies such as disease outbreaks, cancers or indeed for personalized medicines.

Chemokines have been utilised as molecular adjuvants in vaccine formulations and also for cancer immunotherapy. They can activate and mobilise through chemoattraction immune cell subsets to treat disease or enhance immune responses in immunisation (Bobanga et al., 2013). Virus modification of chemokines present unique combination of properties which have utility as vaccine immune modulators or in immunotherapy of diseases such as cancer or in autoimmunity (Vilgelm and Richmond, 2019; Pontejo et al 2018).

SUMMARY OF THE INVENTION

We have identified a human chemokine, from a human chromosomally integrated endogenous form of human herpesvirus 6A (HHV-6A), referred to herein as iciHHV-6A. We have found that the transcript cDNA of a human iciU83A from iciHHV-6A is distinct from the U83A chemokine transcript from circulating free virus HHV-6A, leading to a new chemokine—called iciU83A-N. We show here that iciU83A-N and variants that are described herein can be used as immunogenic adjuvants as well as medicaments.

In a first aspect of the invention, there is provided an isolated polynucleotide comprising or consisting of the nucleic acid sequence of SEQ ID NO: 1 or a variant thereof or sequences complementary thereto and variants thereof. Preferably, the variant comprises a nucleic acid sequence selected from SEQ ID NO: 2, 3, 6, 7, 8 and 9 or a variant thereof.

In another aspect of the invention, there is provided a nucleic acid construct comprising the isolated polynucleotide described above. In a further aspect of the invention, there is provided a host cell comprising the polynucleotide or the nucleic acid construct as described above.

In another aspect of the invention, there is provided an isolated polypeptide comprising the sequence of SEQ ID NO: 4, 5, 14, 15 or a variant thereof.

In a further aspect of the invention, there is provided a pharmaceutical composition comprising the isolated polynucleotide, the nucleic acid construct or the isolated polypeptide described above and a pharmaceutically acceptable carrier.

In another aspect of the invention, there is provided an adjuvant formulation comprising the isolated polynucleotide, the nucleic acid construct or the isolated polypeptide described above.

In a further aspect, there is provided a vaccine or therapeutic composition comprising the isolated polynucleotide, the nucleic acid construct or the isolated polypeptide described above. Preferably, the vaccine or therapeutic composition is selected for treatment of one of cancer, HIV infection or HIV/AIDS, HSV infection, Coronaviruses, Rhinovirus, Alzheimer's and diseases having an autoimmune inflammatory component. In another aspect, there is provided the isolated polynucleotide, the nucleic acid construct, the isolated polypeptide, the pharmaceutical composition or the vaccine or therapeutic composition as described above for use as a medicament.

In a yet further aspect, there is provided, the isolated polynucleotide, the nucleic acid construct, the isolated polypeptide, the pharmaceutical composition or the vaccine or therapeutic composition as described above in the treatment of a disorder characterised by altered levels of one or more of CCR1, CCR4, CCR5, CCR6 and CCR8 or their binding chemokines. Preferably, the disorder is selected from cancer, HSV infection, HIV infection or HIV/AIDS, Coronaviruses, infection, Rhinovirus infection, Alzheimer's and diseases having an autoimmune inflammatory component.

In a further aspect, there is provided there is provided the isolated polynucleotide, the nucleic acid construct, the isolated polypeptide, the pharmaceutical composition or the vaccine or therapeutic composition as described above for use in reducing recurrence of an infection or disease.

In a further aspect, there is provided there is provided the isolated polynucleotide, the nucleic acid construct, the isolated polypeptide, the pharmaceutical composition or the vaccine or therapeutic composition as described above for use in reducing transmission of an infection.

In another aspect of the invention, there is provided a method for the treatment of a disorder characterised by altered levels of one or more of CCR1, CCR4, CCR5, CCR6 and CCR8 or their binding chemokines, the method comprising administering the isolated polynucleotide, the nucleic acid construct, the isolated polypeptide, the pharmaceutical composition, or the vaccine or therapeutic composition described above to a patient in need thereof. Preferably, the disorder is selected from one of cancer, HIV infection or HIV/AIDS, HSV infection, Coronaviruses infection, Rhinovirus infection, Alzheimer's and diseases having an autoimmune inflammatory component. In some embodiments, the disorder is HSV infection, and preferably the HSV infection is acute, reactivated, persistent or latent.

Thus, in one aspect of the invention, there is provided a method of reducing at least one of:

a) acute infection or disease
b) latency of an infection
c) establishment of a latent infection
d) reactivation of an infection or recurrence of disease, and
e) transmission of an infection, the method comprising administering the isolated polynucleotide, the nucleic acid construct, the isolated polypeptide, the pharmaceutical composition, or the vaccine or therapeutic composition as described herein, or variants thereof, to a patient in need thereof.

In a further aspect, there is provided a use of the isolated polynucleotide, the nucleic acid construct, the isolated polypeptide, the pharmaceutical composition or the vaccine or therapeutic composition as described above in the manufacture of a medicament.

In another aspect, there is provided a use of the isolated polynucleotide, the nucleic acid construct, the isolated polypeptide, the pharmaceutical composition or the vaccine or therapeutic composition as described above in the manufacture of a medicament for treatment of a disorder characterised by altered levels of one or more of CCR1, CCR4, CCR5, CCR6 and CCR8 or their ligands, chemokines.

In another aspect, there is provided a use of the isolated polynucleotide, the nucleic acid construct, the isolated polypeptide, the pharmaceutical composition or the vaccine or therapeutic composition as described above in the manufacture of a medicament for treatment of a disorder, wherein the disorder is selected from cancer, HSV infection, HIV infection or HIV/AIDS, Alzheimer's and diseases having an autoimmune inflammatory component. In some embodiments, the disorder is HSV infection, and preferably the HSV infection is acute, reactivated, persistent and/or latent.

In a further aspect, there is provided a use of the isolated polynucleotide, the nucleic acid construct, the isolated polypeptide, the pharmaceutical composition or the vaccine or therapeutic composition as described above in the manufacture of a medicament for reducing recurrence of disease or reactivation of an infection.

In a further aspect, there is provided a use of the isolated polynucleotide, the nucleic acid construct, the isolated polypeptide, the pharmaceutical composition or the vaccine or therapeutic composition as described above in the manufacture of a medicament for reducing transmission of an infection.

In another aspect, there is provided a method of altering the activation of at least one cytokine receptor, the method comprising administering the isolated polynucleotide, the nucleic acid construct or the isolated polypeptide described above to a target cell or to a patient. Preferably, the cytokine receptor is selected from CCR1, CCR4, CCR5, CCR6 and CCR8.

In another aspect, there is provided the use of the isolated polynucleotide, the nucleic acid construct or the isolated polypeptide described above as an immunogenic adjuvant or an immune therapeutic. Preferably, the immunogenic adjuvant or immune therapeutic is selected for treatment of one of cancer, HIV infection or HIV/AIDS, HSV infection, Coronaviruses, Rhinovirus, Alzheimer's and diseases having an autoimmune inflammatory component.

In a further aspect, there is provided a method of identifying a patient that carries integrated iciHHV-6A, expresses the iciU83A gene or iciU83A-N transcript, the method comprising obtaining a nucleic acid sample from a patient and carrying out amplification using the primer pair defined in SEQ ID Nos 10 and 11 and probes or nested primers in SEQ ID Nos 12 and 13.

In another aspect, there is provided a kit for treating a disorder characterised by altered levels of one or more of CCR1, CCR4, CCR5, CCR6 and CCR8, or their binding chemokines, the kit comprising the isolated polynucleotide, the nucleic acid construct, the isolated polypeptide or the pharmaceutical composition described above, together with instructions for treating said disorder.

In a final aspect of the invention, there is provided a kit for identifying a patient that carries integrated iciHHV-6A, expresses the iciU83A gene or iciU83A-N transcript, the kit comprising primers for amplification of the integrated sequence, the primers comprising a sequence as defined in SEQ ID NO: 10 or 11 and probes or nested primers in SEQ ID NOs: 12 and 13.

DESCRIPTION OF THE FIGURES

The invention is further described in the following non-limiting figures:

FIG. 1 shows the nucleic acid and amino acid sequence of an integrated iciHHV-6A iciU83A FIG. 2 shows the DNA sequence of spliced integrated iciHHV-6A U83A. This figure demonstrates our unexpected findings; splicing occurs as shown by cDNA analyses in transient gene expressed cells, through DR, direct repeat, TACC, and non-consensus splice donor/acceptor pairs despite a 3' splice site proximal mutation, TGA-TGG, and that the non-synonymous SNP in the full length gene transforms this spliced product, unlike circulating virus, into mutation of the original spliced stop codon. This unexpectedly now allows read through encoding 8 further amino acids with hydrophobic interactive properties (described in further detail below).

FIG. 3 shows diagnostic primers for detection of integrated iciU83A and iciU83A-N genes and transcripts. A: >integrated iciHHV-6A ciU83Ai diagnostic primer pair and probe/nested primer (atg tcc att cgg ctt ttt att g)gt ttt ttt tat acg gca tat att ggt atg get atc gga (primer pair). B: For detection of the spliced gene, iciU83A-N using nested PCR identification or probe, including derivatives, keeping 3' end 5' tggtccgctgccgtacccgtctgg 3'.

DETAILED DESCRIPTION OF THE INVENTION

Figure 4:
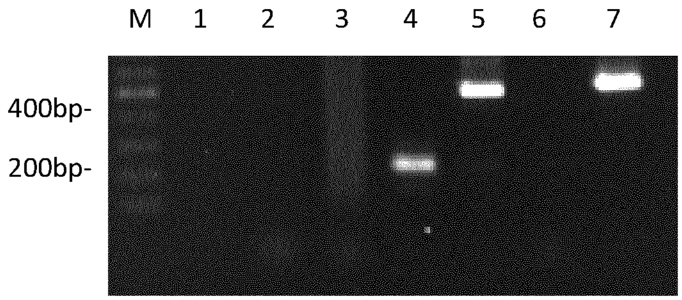
FIG. 4 shows in vitro expression in cells with splicing of iciU83A into iciU83A-N. The gene iciU83A was cloned into a plasmid expression construct and transfected into HEK293 cells. Lanes 1-3 are negative controls, reaction mix with no oligonucleotide primers, reaction mix with oligonucleotide primers, reaction mix with oligonucleotide primers and water only template. Lanes 4-7 are one step RT-PCR reactions of total RNA extracted from the transfected cells primed using primers from the plasmid vector, pCMV (also with primers amplifying the iciU83A gene, not shown). Lanes 5 and 7 are untreated with DNase and show the residual DNA from transfection. Lane 4 and 6 are DNase treated. Lanes 4 and 5 include reverse transcriptase. Lane 5 shows the full length DNA and Lane 4 shows the expressed spliced cDNA product, iciU83A-N.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of biology, microbiology, tissue culture, molecular biology, chemistry, biochemistry and recombinant DNA technology, bioinformatics, which are within the skill of the art. Such techniques are explained fully in the literature.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene" or "gene sequence" is used broadly to refer to a DNA nucleic acid associated with a biological function. Thus, genes may include introns and exons as in the genomic sequence, or may comprise only a coding sequence as in cDNAs, and/or may include cDNAs in combination with regulatory sequences.

The terms "polypeptide" and "protein" are used interchangeably herein and refer to amino acids in a polymeric form of any length, linked together by peptide bonds.

In a first aspect of the invention there is provided an isolated polynucleotide comprising or consisting of a nucleic acid sequence, as defined in SEQ ID NO: 1 or a variant thereof or sequences complementary thereto or a variant thereof. SEQ ID NO: 1 is the cDNA sequence of iciU83A giving iciU83A-N. As used herein, iciU83A-N or variants thereof may be referred to as COLA-N. Such terms may be used interchangeably.

The term "variant" or "functional variant" as used throughout with reference to any of the sequences described herein refers to a variant nucleotide or amino acid sequence or part of the nucleotide or amino acid sequence (such as a fragment) which retains the biological function of the full non-variant sequence. A functional variant also comprises a variant of the sequence of interest, which has sequence alterations that do not affect function, for example in non-conserved residues. Also encompassed is a variant that is substantially identical, i.e. has only some sequence variations, for example in non-conserved residues, compared to the wild type sequences as shown herein and is biologically active. Alterations in a nucleic acid sequence that results in the production of a different amino acid at a given site that does not affect the functional properties of the encoded polypeptide are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Each of the proposed modifications is well within the routine skill in the art, as is determination of retention of biological activity of the encoded products.

As used in any aspect of the invention described throughout a "variant" or a "functional variant" has at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to the non-variant nucleic acid or amino acid sequence described herein. In one embodiment, the variant has 98% or 99% sequence identity to the non-variant sequence.

In an alternative embodiment, a variant may be a sequence that hybridises under stringent conditions to the nucleic or amino acid sequence. By "stringent conditions" or "stringent hybridization conditions" is intended conditions under which a probe will hybridize to its target sequence to a detectably greater degree than to other sequences (e.g., at least 2-fold over background). Stringent conditions are sequence dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Duration of hybridization is generally less than about 24 hours, usually about 4 to 12. Stringent conditions may also be achieved with the addition of destabilizing agents such as formamide.

In one embodiment, the variant has a sequence selected from SEQ ID NO: 2, 3, 6, 7, 8 and 9. SEQ ID NO: 2 has a T to C mutation in the polyT tract of iciU83A-N. SEQ ID NO: 3 is a human codon-optimised form of iciU83A-N. SEQ ID NO: 6 has a T to C mutation in the polyT tract of iciU83A. SEQ ID NO: 7 has mutations in the splice donor and acceptor sites and adjacent TACC direct repeat. SEQ ID NO: 8 has a T to C mutation in the poly T tract, in the splice donor and acceptor sites and in the adjacent TACC direct repeat sequences of iciU83A. SEQ ID NO: 9 is a human codon-optimised form of iciU83A-N that has adjusted mutations in the splice donor and acceptor sites. Variants of one of SEQ ID Nos 2, 3, 6, 7, 8 and 9 are also included in the scope of the invention. Accordingly, in one embodiment of the invention there is provided an isolated polynucleotide sequence comprising or consisting of a nucleic acid sequence as defined in one of SEQ ID Nos 1, 2, 3, 6, 7, 8 and 9 or a variant thereof (a variant is defined above). The above described mutations, in the splice and donor sites lead to stabilisation of iciU83A in the full-length form. Accordingly, in another aspect of the invention, there is provided a method of stabilising iciU83A in the full-length form, the method comprising introducing one or mutations into the splice donor and/or acceptor site of the nucleic acid sequence defined in SEQ ID NO: 1 as shown in FIGS. 1 and 2.

A sequence consisting of SEQ ID NO: 2 is an iciU83A-N mutated variant and may also be referred to as "VTL1", "VTL1-1016" or "VIT1" therein, and these terms can be used interchangeably.

In a further embodiment, the isolated polynucleotide may be a ribonucleotide (RNA) molecule, preferably an mRNA molecule encoding a iciU83A-N protein as defined in SEQ ID NO: 4, 5, 12 or 13 or a variant thereof. The RNA molecule may be modified to avoid detection by the Toll-like receptor, TLR, pathways.

In another embodiment of the invention, the RNA molecule may be administered in the form of a nanoparticle. In one example, the nanoparticle is a liposome-protamine-RNA or LPR. An LPR comprises modified anionic mRNA which is mixed with polycation protamine to generate an mRNA/protamine complex which is then mixed with a liposome (comprising cationic lipid DOTAP and cholesterol) to form an LPR complex which is preferably PEGylated (Wang et al, 2013; Molecular Therapy, 21(2) 358-367). The resulting LPR is small in size (<100 nm) allowing for easy internalisation.

In a further embodiment of the invention, there is provided a nucleic acid construct comprising the isolated polynucleotide described herein. In a preferred embodiment, the nucleic acid construct is a vector, more preferably an expression vector, preferably a recombinant expression vector. Vectors may also include plasmids, cosmids, artificial chromosomes, other virus vectors (i.e. not HHV) and the like. Non-viral vectors may be delivered to a target cell or tissue using transfection. Examples of suitable transfection techniques would be known to the skilled person and include chemical and physical transfection.

In a further embodiment, the polynucleotide sequence is operably linked to a regulatory sequence for gene expression.

The term "operably linked" as used throughout refers to a functional linkage between the promoter sequence and polyadenylation termination sequence to the gene or nucleotide sequence of interest, such that the promoter sequence is able to initiate transcription and termination of the gene or nucleotide sequence of interest.

In a preferred embodiment of the invention, the regulatory sequence is a promoter, more preferably a constitutive promoter such as the cytomegalovirus (CMV) immediate-early promoter. Other suitable promoters would be well-known to the skilled person.

According to all aspects of the invention, the term "regulatory sequence" is used interchangeably herein with "promoter" and all terms are to be taken in a broad context to refer to regulatory nucleic acid sequences capable of effecting expression of the sequences to which they are ligated. The term "regulatory sequence" also encompasses a synthetic fusion molecule or derivative that confers, activates or enhances expression of a nucleic acid molecule in a cell, tissue or organ. The term "promoter" typically refers to a nucleic acid control sequence located upstream from the transcriptional start of a gene and which is involved in the binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression. Also included within the term is a transcriptional regulatory sequence of a classical prokaryotic gene, in which case it may include a −35 box sequence and/or −10 box transcriptional regulatory sequences. For the identification of functionally equivalent promoters, the promoter strength and/or expression pattern of a candidate promoter may be analysed for example by operably linking the promoter to a reporter gene and assaying the expression level and pattern of the reporter gene in various tissue. Suitable well-known reporter genes are known to the skilled person and include for example beta-glucuronidase or beta-galactosidase.

In a further embodiment, the nucleic acid sequence comprises one or more polyadenylation termination sequences, such as from the SV40 virus.

In a further aspect of the invention, there is provided a host cell comprising the nucleic acid construct described herein. The host cell may be prokaryotic or eukaryotic, and may include bacterial cells, fungal cells such as yeast, plant cells, insect cells, or mammalian cells. In a preferred embodiment, the mammalian cell is a human cell. Preferably, the host cell expressed the polynucleotide described herein.

In another aspect of the invention, there is provided an isolated polypeptide comprising or consisting of an amino acid sequence as defined in SEQ ID NO: 4, 5, 14 or 15 or a variant thereof. Preferably, the polypeptides of the present invention are chemokines; alternatively, or in addition, they may act to activate or suppress including as antagonists or agonists to chemokine receptors.

The polypeptides of the present invention may comprise additional amino acids used for purifying encoded protein or for facilitating expression in vivo; for example, N-terminal additions of GS, or of GSRDDDDK, or of GSRIEGR. Other additional sequences may instead be used. The polypeptides of the present invention may include additional sequences useful in purification of the polypeptide; for example, cleavage recognition sequences such as thrombin, enterokinase, or factor Xa recognition sequences.

A further aspect of the present invention provides a method of purifying the polypeptides described herein, the method comprising expressing a vector comprising the nucleotide sequence of SEQ ID NO: 1 or a variant thereof in a host cell, wherein the vector additionally comprises a nucleotide sequence encoding a binding tag; allowing the expressed polypeptide to bind to the target of said binding tag; and causing said bound polypeptide to be released from said target. Preferably the binding tag binds glutathione; the tag may be glutathione S-transferase (GST). The binding tag target is preferably immobilised on a solid support; this allows the bound polypeptide to be easily isolated from unbound product. Other suitable binding tags immobilised on similar solid supports could be used.

The vector may further encode a cleavage recognition site; preferably this site is within or adjacent the binding tag. The recognition site may be for thrombin, enterokinase, or factor Xa, among others. The method may then comprise the step of cleaving the polypeptide at the recognition site.

The polynucleotides, nucleic acid constructs and polypeptides of the present invention may be useful as cytokines, and in particular, as agonists or antagonists of cytokine receptors. Thus, according to a further aspect of the present invention there is provided a method of preventing the activation of (i.e. antagonising) or activating (i.e. agonising) one or more cytokine receptor, the method comprising administering an isolated polynucleotide, nucleic acid construct or polypeptide as to a target cell or to a patient. In one embodiment, there is provided a method of antagonising one or more cytokine receptor, the method comprising administering an isolated polynucleotide or nucleic acid construct comprising a nucleic acid sequence selected from SEQ ID NO: 1, 2 or 3, or an isolated polypeptide selected from SEQ ID NO: 4 or 5. Alternatively, expression of the full-length gene product inhibits expression of the antagonist giving an agonist activity of the receptors or stopping the activity of suppressor T cell subsets which express the cognate chemokine receptors. Accordingly, in an alternative embodiment, there is provided a method of agonising one or more cytokine receptor, the method comprising administering an isolated polynucleotide or nucleic acid construct comprising a nucleic acid sequence selected from SEQ ID NO: 6, 7, 8 or 9 or an isolated polypeptide selected from SEQ ID NO: 14 or 15 and variants thereof. Of note, SEQ ID NO: 6 encodes a mixture of spliced and full-length product (iciU83A-N/iciU83A).

The cytokine receptor to be stimulated or repressed or antagonised or agonised is preferably selected from one or more of CCR1, CCR4, CCR5, CCR6, and CCR8.

In view of the above, the polynucleotides, nucleic acid constructs and polypeptides of the invention can be used to enhance the delivery of vaccines, preferably nucleic acid vaccines, by recruiting cells expressing CCR1, CCR4, CCR5, CCR6 and/or CCR8 to mediate immune responses. In other words, the polynucleotides and polypeptides of the invention can be used to enhance the antigenicity of co-delivered polypeptides or DNA encoding polypeptides (i.e. antigens). These can be used to treat prophylactically or therapeutically alongside vaccines for infectious disease or therapeutic vaccines for cancer or autoimmune conditions.

In one embodiment, the infectious disease is herpes simplex virus types 1 and 2, human immunodeficiency virus, human coronavirus, such as SARS-CoV2 or SARS-like viruses, human cytomegalovirus, coronavirus or hepatitis virus B and C. In another embodiment, the cancer is a solid tumour such as prostate cancer, breast cancer or lymphomas. In a further embodiment, the autoimmune condition is rheumatoid arthritis or chronic obstructive pulmonary disease.

Accordingly, in a further aspect of the invention, there is provided an adjuvant formulation comprising an isolated polynucleotide, nucleic acid construct or polypeptide of the invention or a variant thereof. Also provided is the use of the adjuvant formulation with a vaccine antigen. An adjuvant is a material that when used in conjunction with a vaccine antigen enhances the immune response to the vaccine antigen. Vaccine adjuvants improve the body's immune response and often allow for smaller amounts of an inactivated virus or bacterium to be used in a vaccine.

Therefore, in a further aspect of the invention, there is provided a vaccine or therapeutic composition, comprising an isolated polynucleotide, nucleic acid construct or polypeptide of the invention or a variant thereof (as an immunogenic adjuvant) and a vaccine antigen, where the vaccine antigen can be against any antigen. The vaccine antigen can be a DNA, RNA or peptide vaccine, although in a preferred embodiment, the antigen is encoded by a nucleotide sequence (i.e. the vaccine is a DNA vaccine). The use of a polypeptide comprising the amino acid sequence of SEQ ID NO 4, 5, 14 or 15 or a variant or derivative thereof, or a polynucleotide encoding such a polypeptide in the preparation of a vaccine is also provided. The terms "vaccine composition" and "therapeutic composition" are interchangeable herein.

A vaccine or therapeutic composition for use in accordance with the present invention is capable of inducing a protective immune response in the subject or patient to whom it is administered. An immune response may be induced against any undesirable infectious agent or suitable antigen, such as an antigen that is present on or in a pathogen. The vaccine may therefore be a vaccine against a pathogen, such as a vaccine against a virus, bacterium, fungus, other prokaryotic or eukaryotic cell or organism, or against any protein, glycoprotein or other molecule or structure that can be used to target any such pathogen. Typically, the disease is caused by a pathogen, e.g. a bacterial or viral infection. For example, a viral infection may be an infection caused by a species of Herpesviridae, and in particular could be an infection caused by a human herpesvirus, which includes HSV1 (also known as Herpes Simplex Virus 1), HSV2 (also known as Herpes Simplex Virus 2), HHV3 (also known as Varicella Zoster Virus), HHV4 (also known as Epstein-Barr Virus), HHV5 (also known as Cytomegalovirus), HHV6A/B, HHV7 or HHV8 (also known as Kaposi's Sarcoma-associated Herpesvirus). For example, in the case of HSV2 (human simplex virus type 2), the vaccine antigen formulation may contain sequences encoding a known immunogen glycoprotein D (gD) of HSV2 as described in Example 2. A suitable vaccine or therapeutic composition may be any composition capable of inducing a protective immune response in the subject to whom it is administered.

Typically, a vaccine as described herein is used in a method of treatment, such as a method of treatment by therapy or prophylaxis to prevent or treat disease, in particular infectious disease. A vaccine or therapeutic composition may comprise one or more active therapeutic components, such as viral, peptide, protein based, cell-based and/or nucleic acid based products, such as live viral vaccines, live bacterial vaccines, killed or inactivated viral or bacterial vaccines, vectors encoding an antigen of interest.

Vaccines according to the invention may be formulated for mucosal skin administration or intranasal, intramuscular or intradermal administration or other delivery methods. Vaccines according to the invention may be delivered in a single administration, two administrations or three administrations at intervals of between 2 weeks and 12 weeks apart. For example, the interval may be 2 weeks, 3 weeks, 4 weeks, 2 months or 3 months. In addition, vaccines according to the invention may be administered as an annual "booster" vaccine at 12 monthly intervals after an initial administration.

Immune therapeutics regulate immune cells to sites of immunisation. They can increase or decrease the chemoattraction as chemotactic cytokines, chemokines, as agonist or antagonist of CCR1, CCR4, CCR5 or CCR6. Immune therapeutics according to the invention may be formulated for mucosal skin administration or intranasal, intramuscular or intradermal administration or other delivery methods. Immune therapeutics according to the invention may be delivered in a single administration, two administrations or three administrations at intervals of between 2 weeks and 12 weeks apart. For example, the interval may be 2 weeks, 3 weeks or 4 weeks or 2 or three months. In addition, therapeutics according to the invention may be administered as an annual "booster" vaccine at 12 monthly intervals after an initial administration.

In another aspect of the invention, there is provided a pharmaceutical composition comprising an isolated polynucleotide, nucleic acid construct or polypeptide of the invention or a variant thereof and a pharmaceutically acceptable carrier. The term "carrier" refers to a diluent, adjuvant, excipient or vehicle with which the active ingredient is administered. Suitable pharmaceutical carriers are described in "Remington's Pharmaceutical Sciences" by E. W. Martin, 1995. Examples of pharmaceutical compositions include any solid (tablets, pills, capsules, granules, etc.) or liquid (solutions, suspensions, emulsions, etc.) compositions for oral, topical or parenteral administration.

In another aspect of the invention, there is provided an isolated polynucleotide, nucleic acid construct, polypeptide or pharmaceutical composition or variants thereof as described herein for use as a medicament.

In a further aspect of the invention, there is provided the use of an isolated polynucleotide, nucleic acid construct, polypeptide, pharmaceutical composition, or vaccine or therapeutic composition or variants thereof as described herein in the manufacture of a medicament.

In another aspect of the invention, there is provided an isolated polynucleotide, nucleic acid construct, polypeptide, pharmaceutical composition, or vaccine or therapeutic composition or variants thereof as described herein for use in the treatment of a disorder characterised by altered levels, preferably elevated levels of one or more of the following chemokine receptors: CCR1, CCR4, CCR5, CCR6 and CCR8 or their chemokine ligands.

In another aspect of the invention, there is provided a method of treating a disorder characterised by altered levels, preferably elevated levels of one or more of the following chemokine receptors CCR1, CCR4, CCR5, CCR6 and CCR8 or their chemokine ligands, wherein the method comprises administering the isolated polynucleotide, nucleic acid construct, polypeptide, pharmaceutical composition or vaccine or therapeutic composition, or variants thereof as described herein to a patient in need thereof.

In yet another aspect of the invention, there is provided a use of the isolated polynucleotide, the nucleic acid construct, the isolated polypeptide, the pharmaceutical composition or the vaccine or therapeutic composition as described above in the manufacture of a medicament for treatment of a disorder characterised by altered levels of one or more of CCR1, CCR4, CCR5, CCR6 and CCR8 or their ligands, chemokines.

In a further preferred embodiment, the disorder is selected from one of cancer, such as solid tumours, lymphomas and haematological proliferations or malignancy, HIV infection or HIV/AIDS, HSV infection (human simplex virus, HSV1 and HSV2), Coronaviruses, Alzheimer's and diseases having an autoimmune inflammatory component, such as multiple sclerosis, rheumatoid arthritis, asthma, diabetes, lupus, transplant rejection, atherosclerosis, chronic obstructive pulmonary disease (COPD) or inflammatory bowel disease. Where the disorder is cancer, the medicament, can be used as an intratumoural medicament, whereby administration of the medicament will mediate immune cell traffic to the lesion for clearance (agonist or antagonist activity to cells bearing receptors CCR4, CCR5, CCR6 and CCR8). The same principal can be applied to the other conditions recited herein. Where the disorder is an infection, preferably the infection is acute, reactivated, persistent and/or latent. Virus reactivation can give rise to recurrent disease. By acute infection is meant the primary infection in which symptoms develop over a short time period after infection (e.g. less than six months) to cause disease in a host, and may be resolved by immune system of the host to undetectable levels. By reactivated recurrent infection is meant an infection that may persist in a host for a longer time period (e.g. more than six months), after the acute or primary infection has cleared, then the virus may be reactivated and may cause pathology and/or symptoms, a recurrence, in a host after a period of latency. By latent is meant an infection that is hidden, inactive or dormant, which can be in specific tissue, or in other words, an infection that does not produce visible signs of infection or a disease but may later reactivate in the host to give a persistent infection, cause disease or transmit to another host. In particular, the infection may be a viral infection, and further still it may specifically be a HSV infection.

The data disclosed herein demonstrate that acute, reactivated, persistent and latent infections can be treated under the scope of the invention. For example, FIGS. 6 to 8 demonstrate a reduction in acute infection and acute disease, FIGS. 9 to 12 show a reduction in reactivated infection and recurrent disease and FIGS. 13 to 16 show a reduction in latent infection, which are further described herein. A further advantageous effect of this invention is the provision of a safe treatment, since the experimental data disclosed herein demonstrate that a vaccine or therapeutic composition under the scope of the invention comprising VIT1 (SEQ ID NO: 2) was safe with no adverse effects.

Thus, in another aspect, there is provided a use of an isolated polynucleotide, nucleic acid construct, polypeptide, pharmaceutical composition, or vaccine or therapeutic composition or variants thereof as described herein for reducing an acute infection in a host.

Additionally, in another aspect there is a method for reducing an acute infection in a host, wherein the method comprises administering the isolated polynucleotide, nucleic acid construct, polypeptide, pharmaceutical composition or vaccine or therapeutic composition, or variants thereof as described herein to a patient in need thereof.

In a further aspect, there is a use of the isolated polynucleotide, the nucleic acid construct, the isolated polypeptide, the pharmaceutical composition or the vaccine or therapeutic composition as described above in the manufacture of a medicament for reducing an acute infection.

In particular, the infection may be a viral infection, and further still, it may specifically be a HSV infection.

By reducing acute infection is meant a reduction in the levels of acute infection by up to or more than 10%, 20%, 30%, 40%, 50%, 60%, 70%, 80% or 90% when compared to the level of acute infection prior to treatment or when compared to the level of acute infection in an untreated control (i.e. a negative control) at a given time point.

Figure 6:
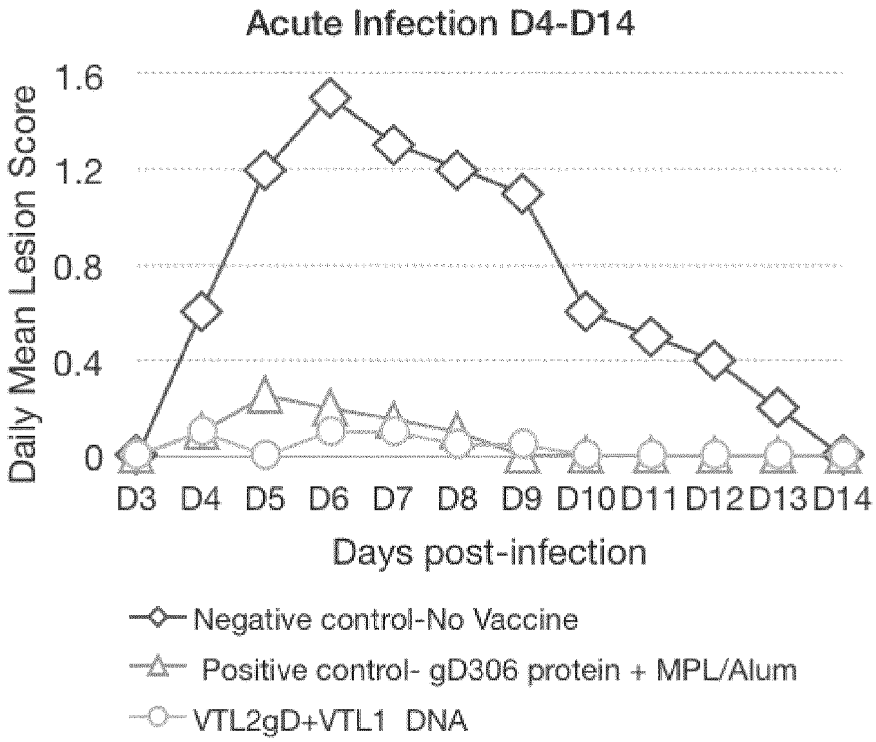
FIG. 6 shows efficacy of iciU83A-N DNA construct in an in vivo preclinical model of HSV2 showing protection from disease from acute infection to 14 days post virus challenge. Here, antigen DNA formulation containing a known immunogen combined with VTL1-1016 (SEQ ID NO: 2). p
Figure 7:
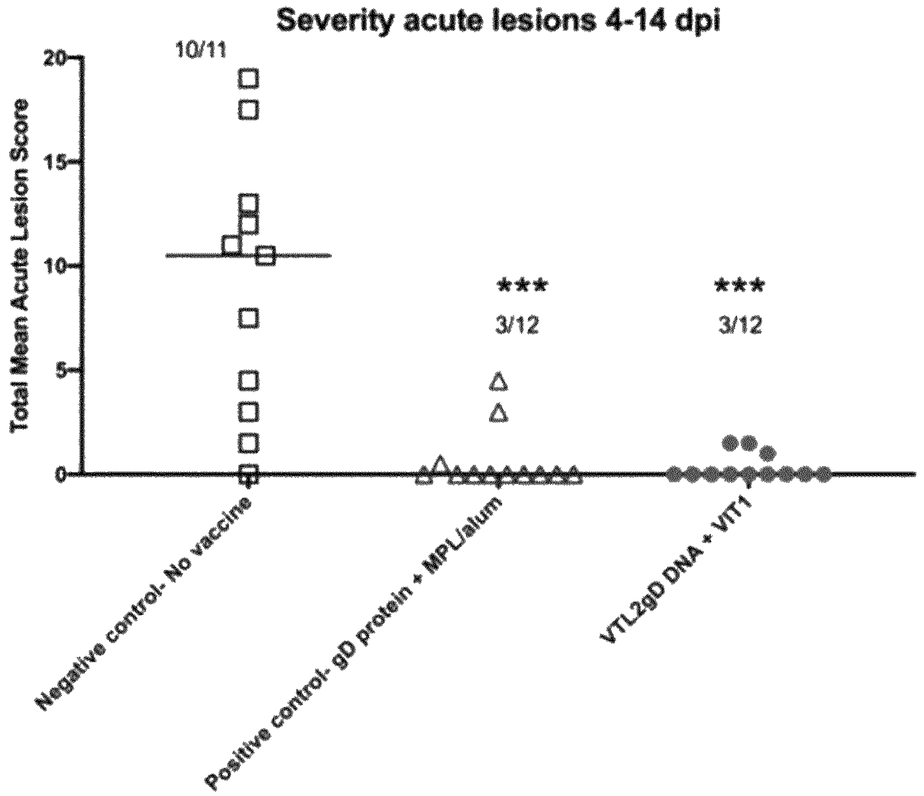
FIG. 7 shows efficacy of iciU83A-N construct, known here as VIT1, in an in vivo preclinical model of HSV2 showing protection in individuals from total severity of disease from acute infection. The total mean acute lesions show total elimination for 75% of the animals. The antigen DNA formulation containing a known immunogen is combined with VIT1-VTL1-1016 (SEQ ID NO: 2).
Figure 8A:
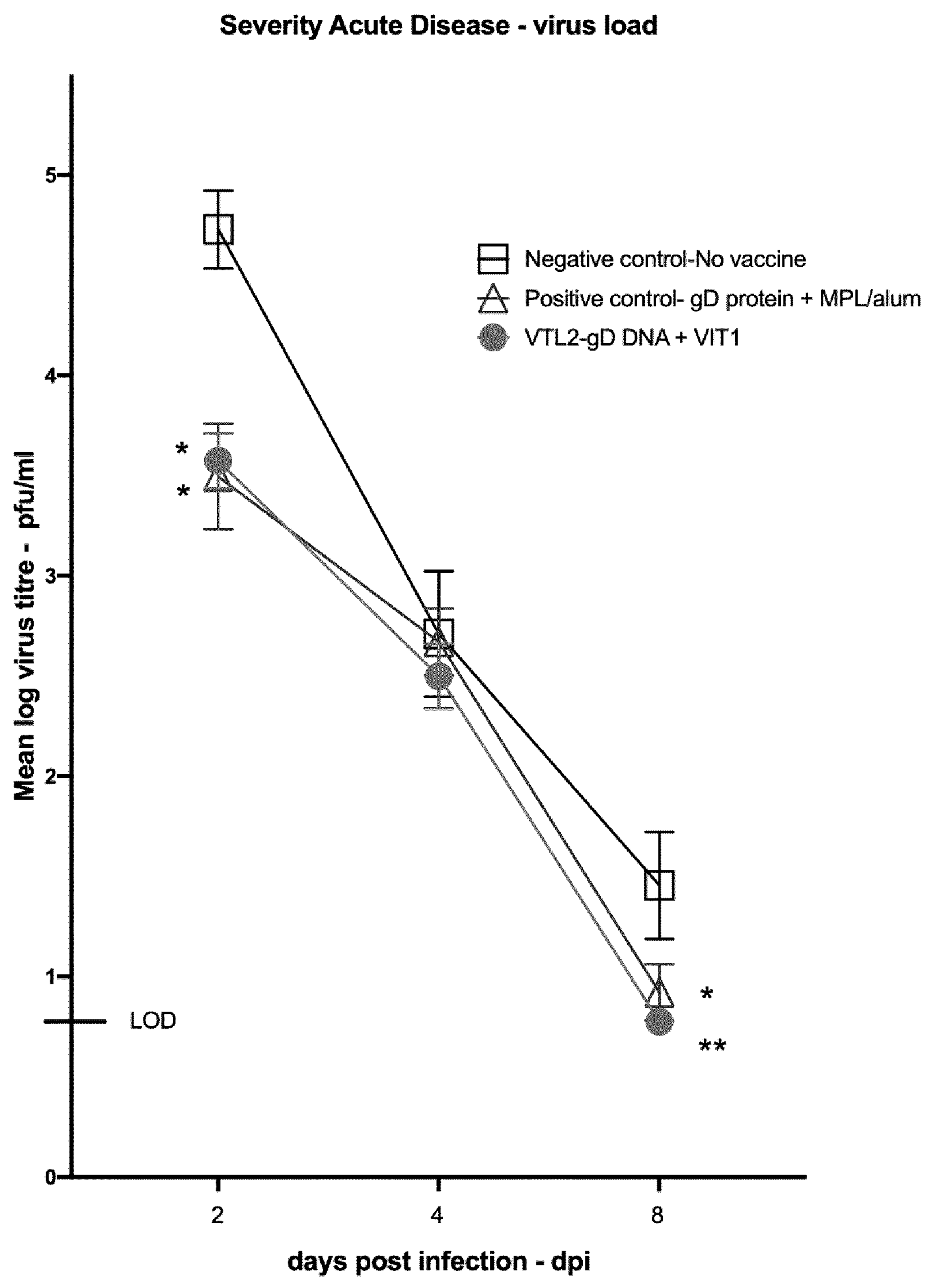
FIG. 8 shows efficacy of iciU83A-N construct, known as VIT1 here, in an in vivo preclinical model of HSV2 showing protection from acute infection. (A) shows a reduction in mean virus load after virus challenge following immunisation. The antigen DNA formulation containing a known immunogen is combined with VIT1-VTL1-1016 (SEQ ID NO: 2). (B) shows significant reduction in virus load in individual animals after virus challenge following immunisation. The antigen DNA formulation containing a known immunogen is combined with VIT1-VTL1-1016 (SEQ ID NO: 2).
Figure 8B:
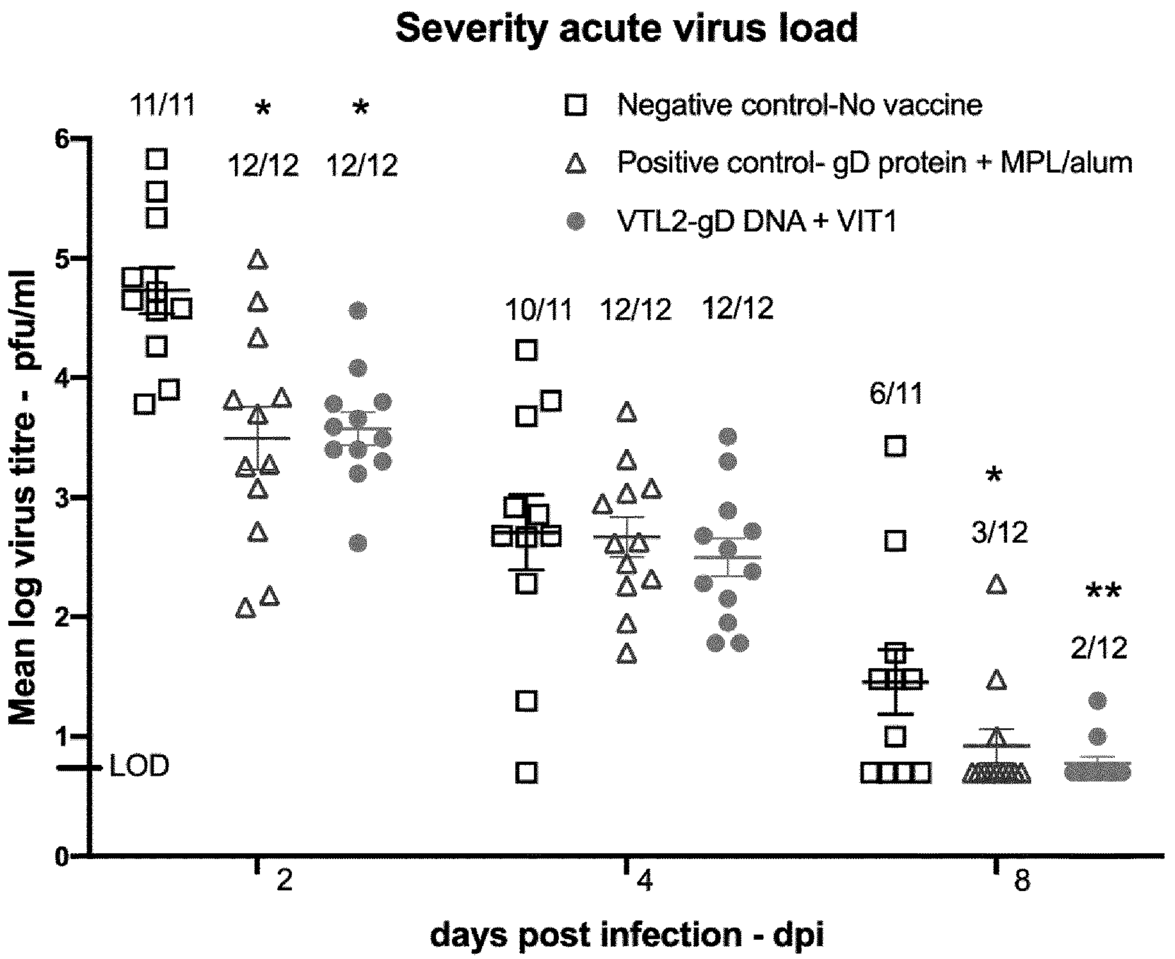

For example, FIG. 6 demonstrates that, at day 6, at the peak of acute infection in the negative control, treatment under the scope of the invention (e.g. VTL2gD and VTL1 DNA) causes a reduction in the daily mean lesion score by over 90% compared to the negative control. Similarly, FIG. 7 shows that treatment under the scope of the invention (e.g. VTL2gD and VIT1 DNA) causes a reduction in the mean severity of acute lesions over a given time course by almost 100% compared to the negative control, and a reduction in the number of individuals suffering from acute lesions by around 70% compared to the negative control. FIG. 8A shows that treatment under the scope of the invention (e.g. VTL2gD and VIT1 DNA) causes a reduction in the viral DNA late at the end of the time course by around 35% compared to the negative control. FIG. 8B shows that treatment under the scope of the invention (e.g. VTL2gD and VIT1 DNA) causes a reduction in the number of individuals with acute virus load by the end of the time course by around 70% compared to the negative control.

Therefore, in another aspect, there is provided a use of an isolated polynucleotide, nucleic acid construct, polypeptide, pharmaceutical composition, or vaccine or therapeutic composition or variants thereof as described herein for reducing the latency of an infection in a host.

Additionally, in another aspect there is a method for reducing latency of an infection in a host, wherein the method comprises administering the isolated polynucleotide, nucleic acid construct, polypeptide, pharmaceutical composition or vaccine or therapeutic composition, or variants thereof as described herein to a patient in need thereof.

In a further aspect, there is a use of the isolated polynucleotide, the nucleic acid construct, the isolated polypeptide, the pharmaceutical composition or the vaccine or therapeutic composition as described above in the manufacture of a medicament for reducing latency of an infection in a host.

In particular, the infection may be a viral infection, and further still, it may specifically be a HSV infection.

By reducing latency is meant a reduction in the levels of latent infection by up to or more than 10%, 20%, 30%, 40%, 50%, 60%, 70%, 80% or 90% when compared to the level of latent infection prior to treatment or when compared to the level of latent infection in an untreated control (i.e. a negative control).

Alternatively, in a further aspect, there is provided the use of an isolated polynucleotide, nucleic acid construct, polypeptide, pharmaceutical composition, or vaccine or therapeutic composition or variants thereof as described herein for preventing the establishment of a latent infection.

Additionally, there is provided a method preventing the establishment of a latent infection, wherein the method comprises administering the isolated polynucleotide, nucleic acid construct, polypeptide, pharmaceutical composition or vaccine or therapeutic composition, or variants thereof as described herein to a patient in need thereof.

Further, there is provided a use of the isolated polynucleotide, the nucleic acid construct, the isolated polypeptide, the pharmaceutical composition or the vaccine or therapeutic composition as described above in the manufacture of a medicament for preventing the establishment of a latent infection.

Figure 14:
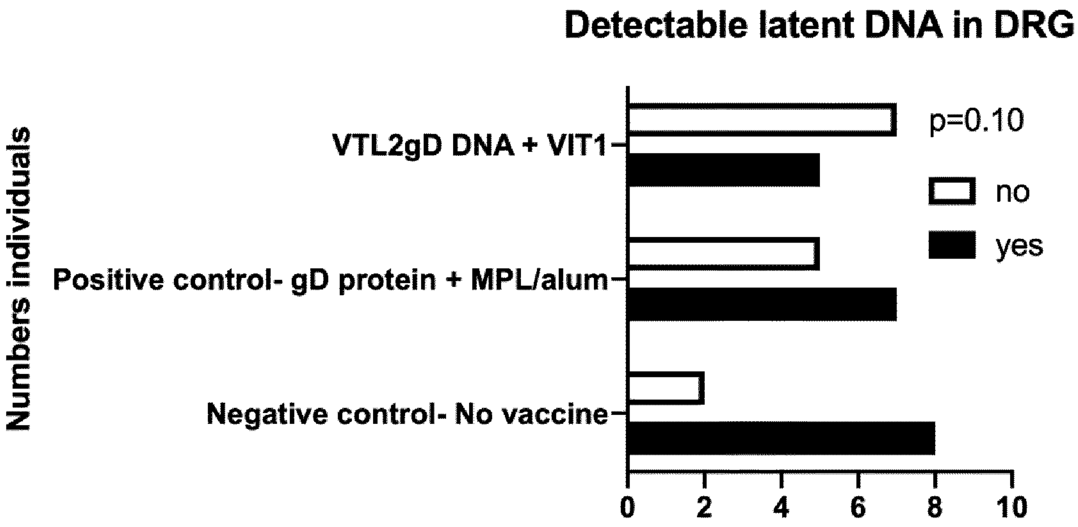
FIG. 14 shows efficacy of iciU83A-N construct, known as VIT1 here, in an in vivo preclinical model of HSV2 showing significant protection in individual animals from establishment of latent infection in the dorsal root ganglia of individual animals, DRG, as measured by quantitative DNA PCR, qPCR. Over half of the animals are protected with no detectable DNA in 58%. The antigen DNA formulation containing a known immunogen is combined with VIT1-VTL1-1016 (SEQ ID NO: 2).
Figure 15:
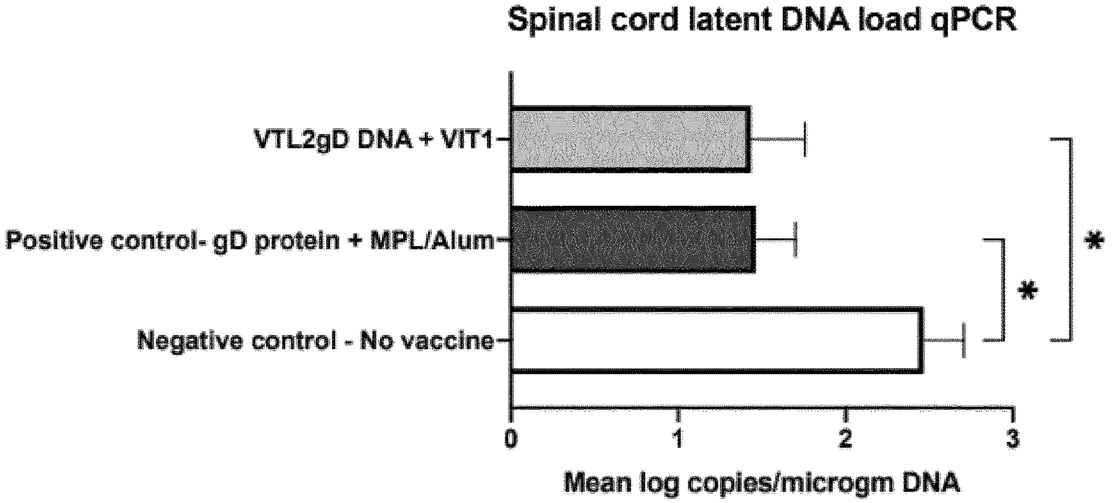
FIG. 15 shows efficacy of iciU83A-N construct, known as VIT1 here, in an in vivo preclinical model of HSV2 showing significant protection from establishment of latent infection in the spinal cord of the animals, halving that detected as measured by quantitative DNA PCR, qPCR. The antigen DNA formulation containing a known immunogen is combined with VIT1-VTL1-1016 (SEQ ID NO: 2).
Figure 16:
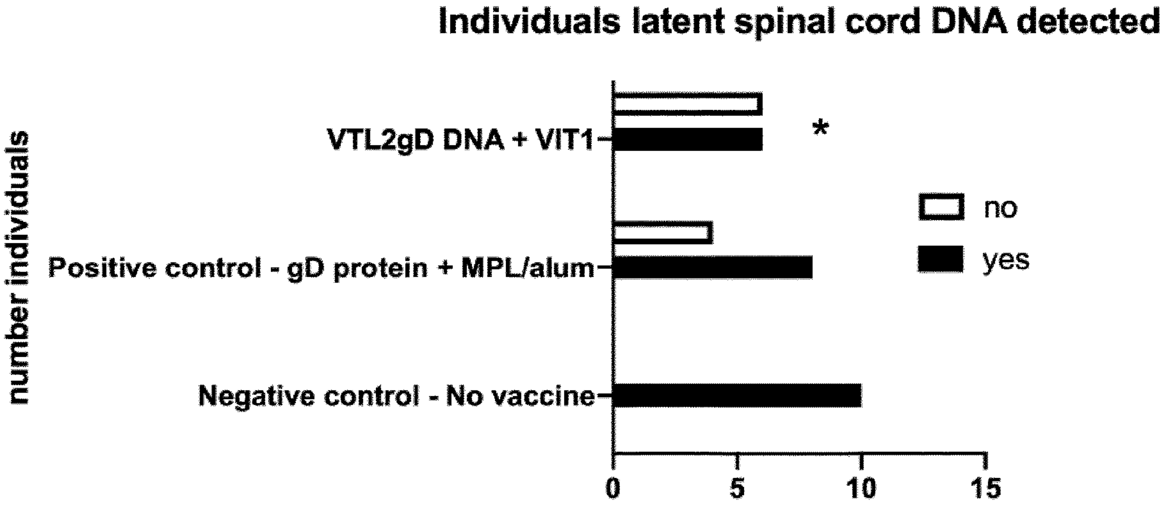
FIG. 16 shows efficacy of iciU83A-N construct, known as VIT1 here, in an in vivo preclinical model of HSV2 showing significant protection in individual animals from establishment of latent infection in the spinal cord of individual animals, as measured by quantitative DNA PCR, qPCR. Half of the animals are protected with no detectable DNA in 50%. The antigen DNA formulation containing a known immunogen is combined with VIT1-VTL1-1016 (SEQ ID NO: 2).

By preventing establishment of latent infection is meant a reduction in the levels of latent infection by up to or more than 10%, 20%, 30%, 40%, 50%, 60%, 70%, 80% or 90% when compared to the level of latent infection prior to treatment or when compared to the level of latent infection in an untreated control (i.e. a negative control). Prevention of establishment of latent infection may also include a 100% reduction compared to the untreated or negative control, thus may include the absence of detectable latent DNA, suggesting the eradication of latent infection. For example, FIGS. 13 and 14 disclosed herein demonstrate that treatment under the scope of the invention provides a decrease in viral DNA at the dorsal root ganglia compared to the negative control and FIGS. 15 and 16 show this is also the case at the spinal cord.

Figure 13:
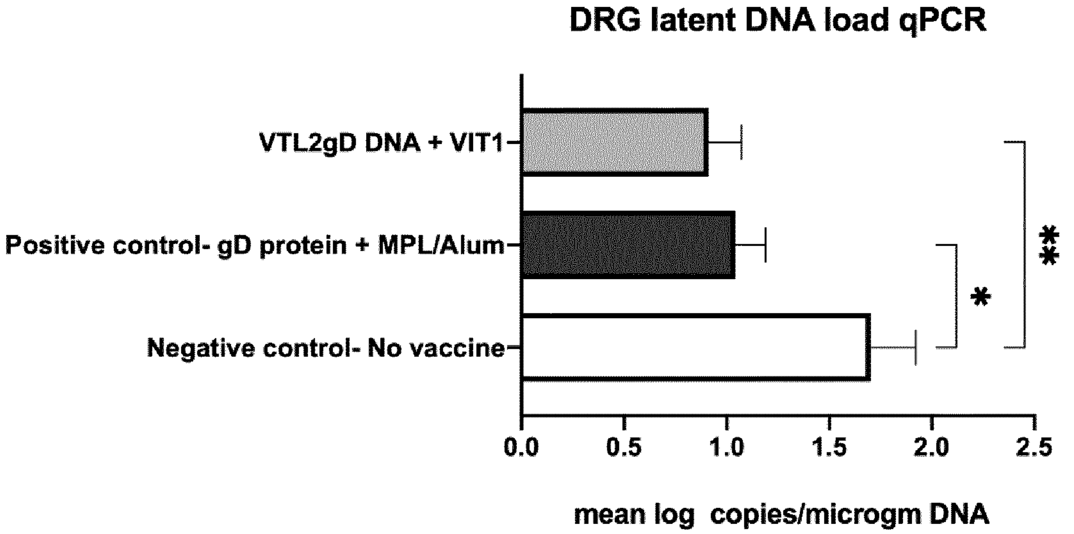
FIG. 13 shows efficacy of iciU83A-N construct, known as VIT1 here, in an in vivo preclinical model of HSV2 showing significant protection from establishment of latent infection in the dorsal root ganglia of the animals, DRG, halving that detected as measured by quantitative DNA PCR, qPCR. The antigen DNA formulation containing a known immunogen is combined with VIT1-VTL1-1016 (SEQ ID NO: 2).

In particular, FIG. 13 demonstrates that treatment under the scope of the invention (i.e. VTL2gD DNA plus VIT1) gives rise to a reduction of latent DNA load at the dorsal root ganglion to approximately 50% of the level in the negative control. FIG. 14 demonstrates that treatment under the scope of the invention (i.e. VTL2gD DNA plus VIT1) gives rise to a reduction in the number of individuals with detectable latent DNA at the dorsal root ganglion, and in particular shows that four times as many individuals had undetectable levels of DNA at the dorsal root ganglion compared to the negative control. FIG. 15 demonstrates that treatment under the scope of the invention (i.e. VTL2gD DNA plus VIT1) gives rise to approximately 40% reduction in the level of latent DNA detected in the spinal cord compared to the negative control. FIG. 16 demonstrates that treatment under the scope of the invention (i.e. VTL2gD DNA plus VIT1) gives rise to a reduction in the number of individuals with detectable latent DNA at spinal cord, and in particular shows that around 50% of individuals had undetectable levels of DNA in the spinal cord after treatment under the scope of the invention compared to none of the negative control individuals.

In one aspect of the invention, there is provided is provided the use of an isolated polynucleotide, nucleic acid construct, polypeptide, pharmaceutical composition, or vaccine or therapeutic composition or variants thereof as described herein for reducing reactivation of an infection or recurrence of disease in those already affected.

In another aspect of the invention, there is provided a method of reducing reactivation of an infection or recurrence of disease, wherein the method comprises administering the isolated polynucleotide, nucleic acid construct, polypeptide, pharmaceutical composition or vaccine or therapeutic composition, or variants thereof as described herein to a patient in need thereof.

In a further aspect, there is a use of the isolated polynucleotide, the nucleic acid construct, the isolated polypeptide, the pharmaceutical composition or the vaccine or therapeutic composition as described above in the manufacture of a medicament for reducing reactivation of an infection or recurrence of disease.

Preferably, the infection is a viral infection, and further preferably this may be a HSV infection.

By reducing reactivation of an infection or recurrence of disease is meant a reduction in the levels of reactivation of an infection or recurrence of disease by up to or more than 10%, 20%, 30%, 40%, 50%, 60%, 70%, 80% or 90% when compared to the level of recurrent infection prior to treatment or when compared to the level of recurrent infection in an untreated control (i.e. a negative control).

For example, a reduction of reactivation of an infection or recurrence of disease may be measured in an in vivo model of viral infection or disease, such as but not limited to the model of HSV infection and disease as disclosed herein. In particular reduction of recurrence as reactivated infection and recurrent disease may be measured by a reduction in the severity of recurrent lesions, a reduction in recurrent viral DNA shedding (by load or occurrence), and/or by a reduction in latent DNA in the dorsal root ganglion or spinal cord (by load or occurrence). However, other suitable models will be known to the skilled person.

Figure 9:
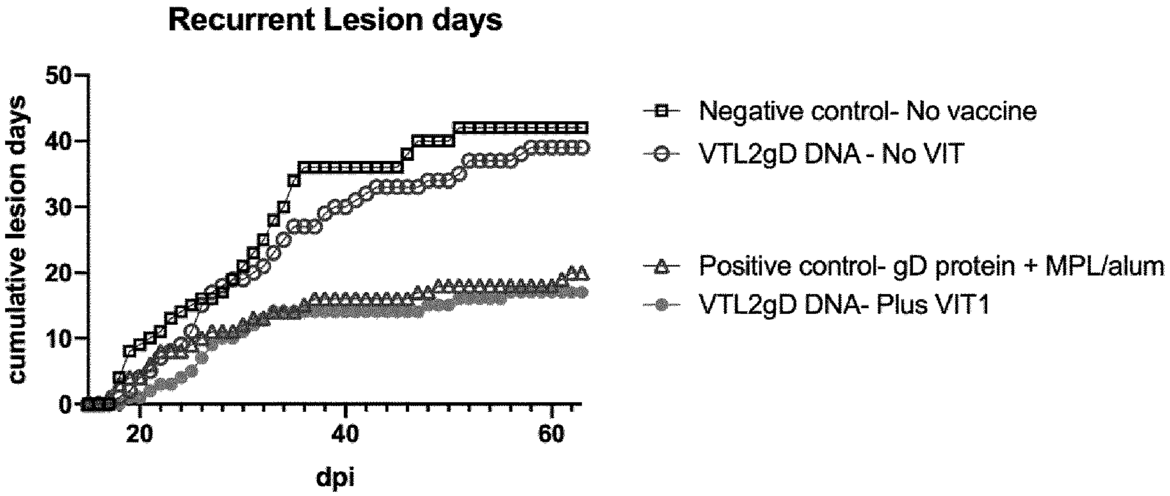
FIG. 9 shows efficacy of iciU83A-N construct, known as VIT1 here, in an in vivo preclinical model of HSV2 showing protection from recurrent disease, with significant reduction in recurrent disease shown by cumulative recurrent lesion days in all animals after virus challenge following immunisation. The antigen DNA formulation containing a known immunogen is combined with VIT1-VTL1-1016 (SEQ ID NO: 2). Protection from recurrences in comparison to no vaccine treatment, is only shown with the VIT1 (SEQ ID NO:2) combination, but not with the VIT1 removed.
Figure 10:
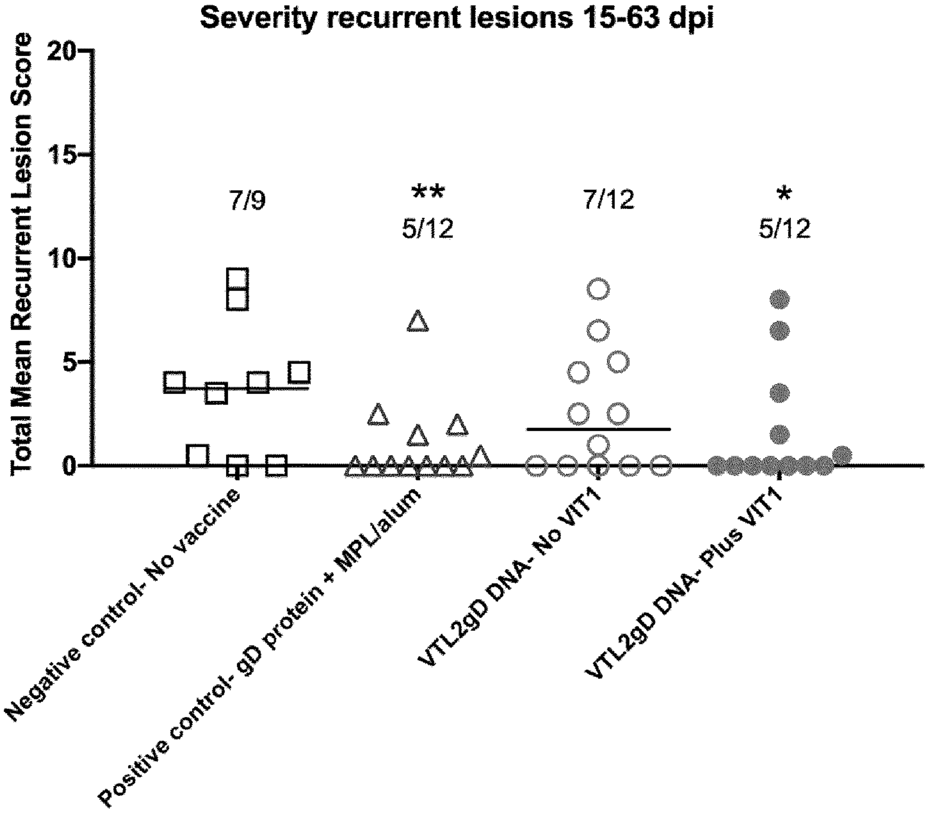
FIG. 10 shows efficacy of iciU83A-N construct, known as VIT1 here, in an in vivo preclinical model of HSV2 showing protection from recurrent disease, with significant reduction in recurrent disease shown in individual animals as total severity of lesions which have recurred days 15-63 after virus challenge following immunisation. The antigen DNA formulation containing a known immunogen is combined with VIT1-VTL1-1016 (SEQ ID NO: 2). Significant protection from recurrences in comparison to no vaccine treatment, is only shown with the VIT1 (SEQ ID NO: 2) combination, but not with the VIT1 removed.

As described above, FIGS. 13-16 demonstrate that treatment under the scope of the invention reduces latent infection, which can lead to reactivation of an infection or recurrence of disease. In addition, FIGS. 9 and 10 demonstrate a reduction in recurrent lesions indicative of a reactivation of an infection and recurrence of disease. In particular, FIG. 9 shows that treatment under the scope of the invention (i.e. VTL2gD DNA plus VIT1) causes a reduction in the number of days with recurrent lesions by around 60% by the end of the time course compared to the negative control. FIG. 10 shows that treatment under the scope of the invention (i.e. VTL2gD DNA plus VIT1) causes a reduction in the total mean current lesion score by around 40% by the end of the time course compared to the negative control.

Figure 11:
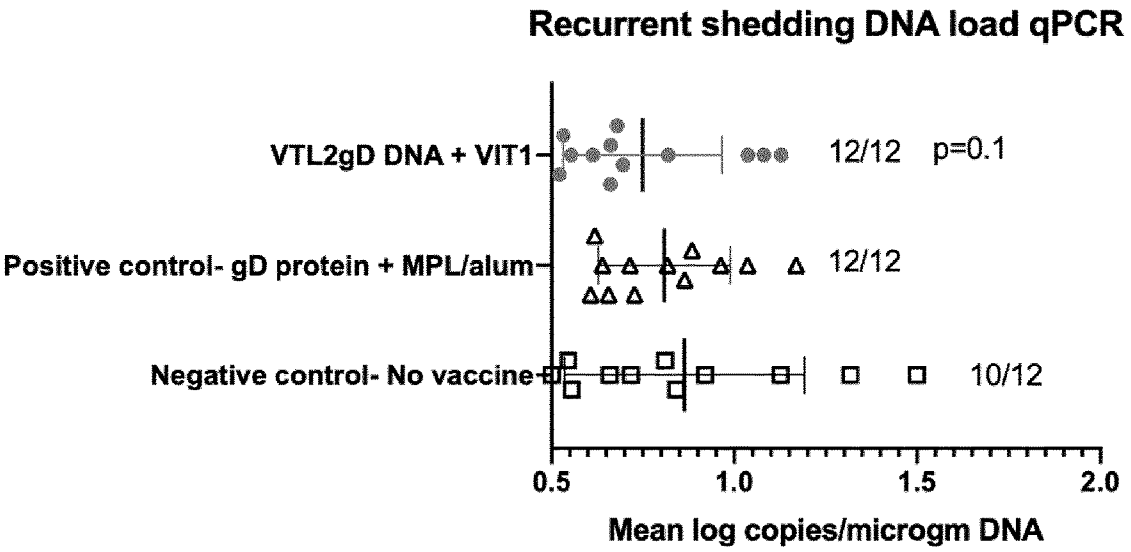
FIG. 11 shows efficacy of iciU83A-N construct, known as VIT1 here, in an in vivo preclinical model of HSV2 showing protection from asymptomatic recurrent shedding virus, total recurrences in all animals, as measured by quantitative DNA PCR, qPCR. The antigen DNA formulation containing a known immunogen is combined with VIT1-VTL1-1016 (SEQ ID NO: 2).
Figure 12:
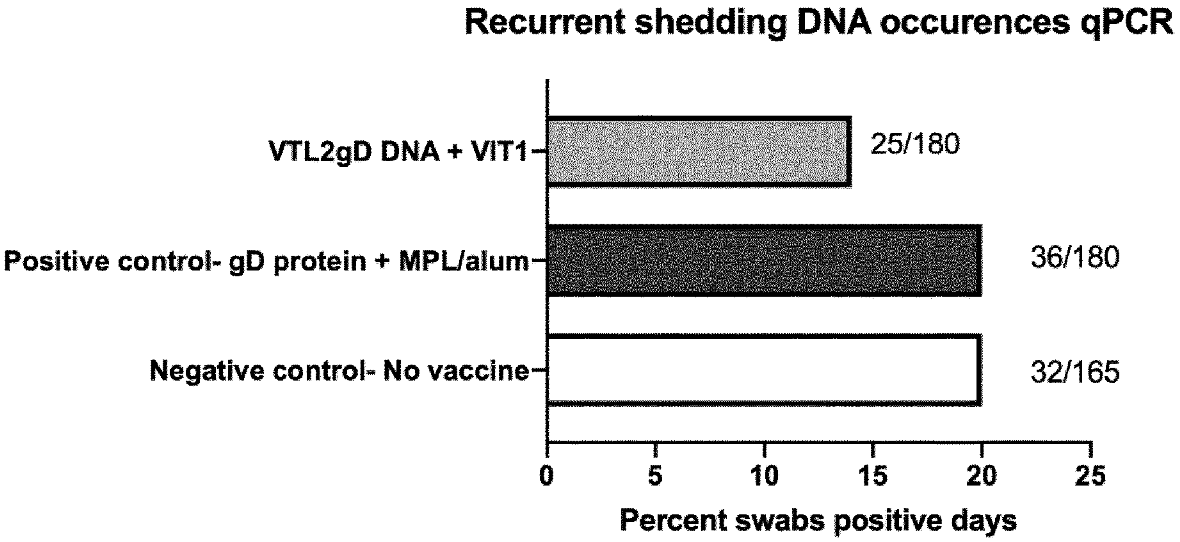
FIG. 12 shows efficacy of iciU83A-N construct, known as VIT1 here, in an in vivo preclinical model of HSV2 showing trend for protection from asymptomatic recurrent shedding virus, total recurrences in individual animals, with the mean shown, as measured by quantitative DNA PCR, qPCR. The antigen DNA formulation containing a known immunogen is combined with VIT1-VTL1-1016 (SEQ ID NO: 2).

Further still, FIGS. 11 and 12 demonstrate that treatment under the scope of the invention reduces the level of recurrent shedding, which is also indicative of a recurrent reactivated infection. For example, FIG. 11 shows that treatment under the scope of the invention (i.e. VTL2gD DNA plus VIT1) causes a reduction in the mean recurrent shedding DNA load by around 15% compared to the negative control. FIG. 12 shows that treatment under the scope of the invention (i.e. VTL2gD DNA plus VIT1) causes a reduction in the occurrences of positive swabs for recurrent shedding DNA over the course of the experiment by around 30% compared to the negative control.

In one aspect of the invention, there is provided is provided the use of an isolated polynucleotide, nucleic acid construct, polypeptide, pharmaceutical composition, or vaccine or therapeutic composition or variants thereof as described herein for reducing transmission of an infection. Preferably, the infection is a viral infection.

In another aspect of the invention, there is provided a method of reducing transmission of an infection, wherein the method comprises administering the isolated polynucleotide, nucleic acid construct, polypeptide, pharmaceutical composition or vaccine or therapeutic composition, or variants thereof as described herein to a patient in need thereof. Preferably, the infection is a viral infection.

By transmission is meant the ability of the pathogen causing the infection (for example, a virus or a bacterium) to move from one host to another. For example, a reduction of viral transmission may be measured in a model of viral infection, such as but not limited to the model of HSV infection as disclosed herein, by reduction in recurrent reactivated viral DNA shedding (by load or occurrence), and/or by a reduction in establishment of latent DNA in the dorsal root ganglion or spinal cord (by load or occurrence).

By reducing transmission is meant a reduction in the levels of transmission by up to or more than 10%, 20%, 30%, 40%, 50%, 60%, 70%, 80% or 90% when compared to the level of transmission prior to treatment or when compared to the level of transmission in an untreated control (i.e. a negative control). In particular, this may mean the level of shedding is reduced by up to or more than 10%, 20%, 30%, 40%, 50%, 60%, 70%, 80% or 90% when compared to the level of shedding prior to treatment or when compared to the level of shedding in an untreated control (i.e. a negative control).

As explained above, FIGS. 11 and 12 demonstrate that treatment under the scope of the invention (i.e. VTL2gD DNA plus VIT1) causes a reduction in virus shedding, which can cause transmission of the infection.

Thus, in one aspect of the invention, there is provided a method of reducing at least one of:

a) acute infection and disease
b) latency of an infection
c) establishment of a latent infection
d) reactivation of an infection and recurrence of disease, and
e) transmission of an infection, the method comprising administering the isolated polynucleotide, the nucleic acid construct, the isolated polypeptide, the pharmaceutical composition, or the vaccine or therapeutic composition as described herein, or variants thereof, to a patient in need thereof.

Administration of pharmaceutical compositions of the invention may be accomplished orally or parenterally. Methods of parenteral delivery include topical, intra-arterial, intramuscular, subcutaneous, intramedullary, intrathecal, intraventricular, intravenous, intraperitoneal, mucosal or intranasal administration. In addition to the active ingredients, such compositions may comprise suitable pharmaceutically acceptable carriers comprising excipients and other components, which facilitate processing of the active compounds into preparations suitable for pharmaceutical administration.

Pharmaceutical preparations for oral use can be obtained through combination of active compounds with a solid excipient, optionally grinding a resulting mixture, and processing the mixture of granules, after adding suitable additional compounds if desired to obtain tablets or dragee cores. Suitable excipients include carbohydrate or protein fillers such as sugars, including lactose, sucrose, mannitol, sorbitol; starch from corn, wheat, rice, potato, or other plants; cellulose such as methylcellulose, hydroxypropylmethylcellulose, or sodium carboxymethylcellulose; and gums including arabic and tragacanth; as well as proteins such as gelatin and collagen. If desired, disintegrating or solubilising agents may be added, such as cross-linked polyvinyl pyrrolidone, agar, alginic acid, or a salt thereof.

Dragee cores can be provided with suitable coatings such as concentrated sugar solutions, which may also contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for product identification or to characterise the quantity of active compound.

Pharmaceutical preparations, which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally stabilisers. In soft capsules, the active compounds can be dissolved or suspended in suitable liquids, such as fatty oils, liquid paraffin, or liquid polyethylene glycol with or without stabilisers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous suspension injections can contain substances, which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension can also contain suitable stabilisers or agents, which increase the solubility of the compounds to allow for the preparation of highly concentrated solutions.

For topical or nasal administration, penetrants appropriate to the particular barrier to be permeated may be used in the formulation.

The pharmaceutical compositions of the present invention can be manufactured substantially in accordance with standard manufacturing procedures known in the art.

In another aspect of the present invention, the isolated polynucleotide, nucleic acid construct, polypeptide or pharmaceutical composition or variants thereof as described herein may form part of a combination therapy. In one embodiment, there is provided a method of treatment of HIV infection and/or HIV/AIDS comprising administering the isolated polynucleotide, nucleic acid construct, polypeptide or pharmaceutical composition to a patient in combination with another anti-HIV therapeutic agent. By HIV therapeutic agent, is meant a drug or vaccine or other agent useful in therapy. The combination may be synergistic. The isolated polynucleotide, nucleic acid construct, polypeptide or pharmaceutical composition, may be provided as part of the same medicament or as a separate medicament for administration at the same time or different time as the other anti-HIV therapeutic agent.

The invention also provides the isolated polynucleotide, nucleic acid construct, polypeptide or pharmaceutical composition or variants thereof as described herein for use in the treatment of HIV, wherein said isolated polynucleotide, nucleic acid construct, polypeptide or pharmaceutical composition is used in a synergistic combination with another anti-HIV therapeutic agent.

The other anti-HIV therapeutic agent according to the invention may be selected from a HIV replication inhibitor, an HIV vaccine or an HIV entry inhibitor such as a peptide or nucleotide sequence encoding peptide or small molecule drug, which blocks infection through CCR5 co-receptor or other HIV receptors.

The invention still further provides a method of treating bacterial infections, comprising administering an isolated polynucleotide, nucleic acid construct, polypeptide or pharmaceutical composition or variants thereof as described herein to a patient. The invention also provides the use of an isolated polynucleotide, nucleic acid construct, polypeptide or pharmaceutical composition or variants thereof as described herein in the preparation of an antibacterial composition. An antibacterial composition comprising an isolated polynucleotide, nucleic acid construct, polypeptide or pharmaceutical composition or variants thereof as described herein is also provided.

In another aspect of the invention, there is provided a method of identifying a patient that carries integrated iciHHV-6A or expresses the iciU83A gene and iciU83A-N transcript, the method comprising obtaining a nucleic acid sample from a patient and carrying out amplification using the primer pair defined in SEQ ID Nos 10 and 11. This can be used to stratify patient groups in testing or treating with the iciU83A and iciU83A-N genes in expression constructs used in nucleic acid vaccines or as encoded polypeptides. These can also be used to follow expression of the genes in vitro cellular expression to quantify and in vivo expression to quantify and localise expression in relation to protective effects and to monitor delivery. In patients treated with the iciU83A or iciU83A-N genes or polypeptides, these diagnostic primers can be used to follow delivery, expression, localisation and stability. These features can then be diagnostic of efficacy. Critically the diagnostic primers can be used to distinguish the vaccine gene expression from circulating virus. In another aspect of the invention there is provided isolated polynucleotide sequences as defined in SEQ ID Nos 10 or 11, 12 and 13 or variants thereof (a variant is defined above). Also provided is the use of these sequences as primers, which allow the detection of integrated iciHHV-6A as described herein.

Primer and probe sequences are as follows:

For whole gene:

```
                                        SEQ ID NO: 10
5'ATGTCCATTCGGCTTTTTATTG 3'

                                        SEQ ID NO: 11
5'TCATGATTCTTTGTCTAATTTC 3'
```

For detection of the full length gene, iciU83A, and spliced gene iciU83A-N using nested PCR identification or probe, including derivatives, keeping 3' end:

```
                                        SEQ ID NO: 12
5'AAAAAGCTAAAAAGTTGTTCTGCTGCTTACCCGTCTGG 3'

                                        SEQ ID NO: 13
5'TGGTCCGCTGCCGTACCCGTCTGG3'
```

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments, which are described.

The foregoing application, and all documents and sequence accession numbers cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

The invention is now described in the following non-limiting examples.

Example 1

Genomic, In Silico and In Vitro Cellular Expression

The concerns over DNA integration related to observations of integration by homologous recombination using molecular biology technologies and in vitro cell culture as well as replication strategies by certain virus families. Although integration by homologous recombination has been observed in vitro occasionally in genes introduced by cell culture, it is a rare event (approximately 1 in million) and requires strong selection to isolate the transduced cell. In contrast, some viruses use DNA integration as an obligate step of their replicative cycle, therefore integration occurs with each and every replicative cycle. These are the well-known retrovirus family, which include a lentivirus family, including highly characterised HIV. However, these are RNA viruses, which require a virus encoded enzyme, reverse transcriptase, to make a DNA copy of the RNA genomes, which are then integrated into the host genome by another virus encoded enzyme, integrase, as part of the pathway to generate replicative copies of the native RNA, now by host DNA transcription. Therefore, DNA integration is an obligate step of the replication of these viruses. In fact, ancestors of this virus family make up the dominant repetitive DNA families of human host genomes. This shows, that it is indeed the RNA world, rather than DNA gene introduction, which holds most concern for human host genome genetic integration.

Although retroviruses account for the majority of virus DNA introduced into the host genome, this is over large evolutionary time periods. The ancient viral genetic introductions, include virus genomes that encode envelope proteins, which no longer can interact with cellular receptors inside the current human host. This is because they are modelled to have interacted with an ancestral host, which no longer exists. Similar to this principle, is the one DNA virus family with exceptional DNA virus integration. This is the roseoloviruses, with human examples including human herpesvirus A/B, HHV-6A and HHV-6B. These are members of one of the largest DNA viruses, these viruses can establish latency for the lifetime of the host, like other herpesviruses. In general, this herpesvirus latency strategy results in the virus genome maintaining in an episome. In an exception to this rule, roseoloviruses, HHV-6A and HHV-6B, can integrate in the telomeric region of the host genome. This is different from retroviruses, as it does not appear to be an obligate step of its replicative pathway. Instead, this appears to be a form of latency. Again it is not clear if this step in latency occurs during the natural lifecycle of these viruses. What is clear though, is that HHV-6A and B are integrated in approximately 1% of human populations, in roughly equal proportions, 0.2% HHV-6A and 0.4% HHV-6B (Tweedy et al., 2016). These appear ancient events, and have led to Mendellian inherited lineages, making these integrations appear as endogenous virus genomes. While the inherited human chromosomally integrated HHV-6B, iciHHV-6B, genomes appear to co-segregate with circulating virus HHV-6B, the inherited chromosomally integrated HHV-6A, termed iciHHV-6A, genomes appear distinct (Greninger et al., 2018; Tweedy et al., 2015b; Tweedy et al., 2016). These appear to have integrated at an early stage in the dissemination of *Homo sapiens*, with our phylogenetic reconstructions, segregating these genomes distinct from circulating virus and placing the earliest families approximately 250K years ago (unpublished data). Therefore, this is a rare event and also indicates these are distinct genomes. Our analyses by deep next generation sequencing, showed one of the oldest lineages related to an integration event in the telomere of chromosome 17p. Surprisingly, our analyses of the genome showed it had all the genes intact as well as known cis acting sequences required for virus replication. As described herein, the encoded immunomodulatory genes include unexpectedly one with a novel spliced product with distinct properties (as shown in FIG. 2).

The novel result focuses on the central immunomodulator chemokine encoded by gene U83A. In the circulating virus, this encodes a chemokine-like molecule, which can mediate immune cell chemotaxis with a unique specificity via interaction with an array of human chemokine receptors (Catusse et al., 2009; Catusse et al., 2007; Clark et al., 2013; Dewin et al., 2006). This specificity was distinct from that of any other human chemokine or microbial peptide. We hypothesized, that if the integrated genome is from an ancestral virus infecting a homo sapien or hominid ancestor, then the immunomodulatory genes may be distinct. While we found the gene structure was maintained across the genome, in the immunomodulatory gene, chemokine U83A, in iciHHV-6A, iciU83A, (FIG. 1) we unexpectedly discovered that the transcript is distinct (cDNA, FIG. 2) and encodes for altered protein products (FIG. 2).

The circulating virus U83A gene is spliced using non-canonical splice donor and acceptor sites contained within an unusual direct repeat sequence, CT-AC within TACC (French et al., 1999; Tweedy et al., 2015b). In the iciHHV-6A genome these cis acting elements are maintained, but there is a distinct non-synonymous SNP proximal to the provisional splice acceptor site, which affects the acceptor splicing sequence consensus site and as such was placed to disrupt the unusual splicing event (FIG. 1). Moreover, our earlier results had shown evidence for the full length unspliced transcript expressed in two individuals with heart disease and integrated iciHHV-6A (Tweedy et al., 2015b). Therefore, it was not clear whether any splicing event at all occurred at this locus in iciHHV-6A. This is shown in our annotations for the first genome sequence for the iciHHV-6A, where only the full-length gene product is shown (NCBI NC_001664.4 reference genome sequence for HHV-6A and KT895199.1 for iciHHV-6A). Remarkably, although in the virus the full length U83A encodes the full signal sequence resulting in the mature secreted product, actually this is only expressed rarely in circulating virus. This is due to variation in a poly-T tract which disrupts expression of the gene by giving a frame-shift mutations, so the signal sequence is no longer made and the product not secreted. However, in the iciHHV-6A genome, the iciU83A gene is genetically fixed to encode the full signal sequence with a fixed length poly-T tract (Tweedy et al 2015b). Furthermore, it was not clear whether any splicing occurred at this ancestral iciU83A gene. Transcriptomics analyses using RNAseq on circulating virus gene expression, only identified an anti-sense spliced transcript mapping to the U83 loci or restricted gene expression in integrated iciHHV-6A/B genomes, consisting of immediate early genes involved in gene control and not further describing U83A (Peddu et al., 2019). An earlier review on virus chemokines, noted restricted gene expression, also noted lack of splicing U83A in transcripts identified in people harbouring iciHHV-6A genomes, citing our previous genomic analyses citing two iciHHV-6A integrated genomes with only full length transcript expression of U83A detected in two patient donors (Pontejo et al., 2018; Tweedy et al., 2015b).

Surprisingly, our discoveries summarized in this filing here showed, that by investigating the individual gene expression in transfected cells in vitro that the integrated U83A gene (iciU83A), can be expressed and spliced. This was identified by using both genomic prediction and by cDNA analyses of ciU83A gene in expression vectors transfected into cells and then characterised using RT-PCR followed by sequence determination. This showed that despite the previous in vivo and cellular characterisations of iciHHV-6A individuals, and despite the SNP proximal to the splice donor site, that the non-consensus splicing can be utilised (FIG. 2). This mutation, causes a coding mutation from that in the virus from GAT(Asp) to GGT(Gly) (FIGS. 1-3) in the full-length human integrated iciU83A gene. Using thus information we have been able to design diagnostic primers (FIG. 3). Furthermore, we have surprisingly found that this same coding mutation, from the frameshift due to the splicing, now precisely disrupts the spliced stop codon that had led to the truncated version of the virus U83A gene, U83A-N (as it only includes the encoded N-terminal half of the molecule) (FIG. 2). To summarise, this finding is surprising and unexpected for the following reasons:

1. The non-synonymous mutation in the chromosomally integrated gene iciHHV-6A U83A is conserved in all related genomes at this integration site and results in a frame shift mutation after splicing that results in removal of a spliced stop codon and extension of the coding sequence of the spliced gene cDNA of iciHHV-6A U83A-N.

2. This coding extension initiates with one of the rarest codons, encoding tryptophan. 3. The splicing itself is rare non-consensus donor and acceptor sites and includes an unusual direct repeat structure.

4. The non-synonymous mutation is adjacent to the non-consensus donor and acceptor sites and could affect the splicing efficiency.

5. The related virus HHV-6B has also a human chromosomally integrated genome version iciHHV-6B and this does not have the same frame shift, stop codon disrupting, non-synonymous mutation. It has the same structure of spliced product.

In the virus genome, U83A and U83A-N encode respectively, full length and the truncated protein product from the spliced gene (Dewin et al., 2006). These function as paired agonist and antagonist versions of the U83A chemokine and are central to orchestrating immune cell attraction to the virus replicative site for virus dissemination or immune evasion. Surprisingly, in the human chromosomally integrated HHV-6A iciU83A, the spliced product is no longer truncated at this site. Instead, it is now extended to a downstream stop codon and results in an extended truncated product iciU83A-N (FIG. 2). This now has a hydrophobic tag of 8 amino acids (FIG. 2). This can act to associate with the membrane or mediate multimers, both leading to stabilisation and altered presentation. As described above, since this mutation is proximal to the non-consensus splice acceptor site, it was not possible to predict the spliced cDNA without experimental definition as shown here. Indeed, this splice in this gene has not been demonstrated or recorded before.

The spliced product has discrete functional domains. We have previously demonstrated that the encoded N-terminal domain dictates specificity of chemokine receptor interactions (Dewin et al., 2006). This could be delineated to a 17 amino acid peptide region, with the determinant of specificity between CCR2 and CCR5 interactions determined by a single arginine residue (Clark et al., 2013). In the iciU83A-N molecule this N-terminal domain remains intact, representing the receptor specificity as previously defined (FIGS. 1 and 2). In fact, in comparisons of the virus U83A-N spliced molecule to the full length U83A, all the receptor specificity was maintained, only the C-terminal signaling domain was abrogated in the spliced truncated molecule. This functional N-terminal domain is also preserved in the iciU83A-N molecule, the encoded N-terminal binding domain is completely intact, but the C-terminal signaling domain is removed. However, surprisingly and unexpectedly, the iciU83A-N molecule is not only truncated, it has a C-terminal extension of the eight amino acid constituting a hydrophobic extension (FIG. 2). This is composed of an aromatic residue rich domain, which via multiple tryptophan residues can increase membrane association as well as unique multimerisation of the molecule. Such tryptophan 'tagging' experimentally has increased stability and multimerisation of covalently attached peptides as well as disrupting lipid membrane interactions, increasing bacteriocidal activities, and promoting multimerisation (Kamei et al., 2018; Singh et al., 2017; Yau et al., 1998). Therefore, this hydrophobic C-terminal tag in the iciU83A-N encoded molecule provides superior and distinct activities to other virus encoded chemokine molecules. Indeed, the human encoded chemokine fractalkine has two distinct versions and soluble secreted form and a membrane-tethered form. It is this diversity that accounts for its manifold functions in neurobiology as well as cardiology.

The specificity reported derived from the maintained N-terminal domain, includes targeting CCR1, 4, 5, 6 and 8 receptors (Catusse et al., 2009; Catusse et al., 2007; Dewin et al., 2006). This unique combination allows targeting of immunesuppresive T-regulator lymphocytes, particularly via CCR4 and CCR6. The human CCR6 is monospecific for CCL20, therefore expanding receptor interactions including CCR6 is a unique property of the ciU83A-N molecule. The unique application is in ability to act as an antagonist of these receptors. This is because the C-terminally signaling moiety is no longer present. Antagonism of CCR4 in particular has been demonstrated as a novel mechanism for increasing immunity to a target antigen (Bayry et al., 2008) with utility also in uncovering immune-reactivity to tumours by altering the tumour microenvironment (Vilgelm and Richmond, 2019). Blocking immune-suppressors, is a well defined mechanism for application of antibody molecules to oncology. These are antibodies to so-called 'immune checkpoint inhibitors', they are directed either to the receptor or ligand pair of signaling molecules on immunesuppresive T-lymphocytes which normally add 'brakes' to immune signalling, for instance to prevent breaking of immune tolerance and unleashing the damaging self immune responses of an 'autoimmune' reaction. This strategy has been used successfully on terminal cancer patients, however it has inherent safety risks and only works on a minority of patients (<30%) (Konstantina et al., 2019; Kwok et al., 2016), a success rate that would not favour small molecules development, and also demanding additional resources in genetic profiling of patients and their cancers to determine susceptibility to this method via specific receptor expression on the tumours. However, using our discovery of iciU83A-N, its diverse chemokine receptors are expressed on normal host immune cells, and therefore separate from the genetically evolving cancers evading immunity. This enables a new method for treatment for applying immunotherapy to more people.

The iciU83A and iciU83A-N genes have some unusual cis acting features. We had shown previously that the virus U83A gene has a poly-T motif towards the N-terminal encoding region. This gives rise to instability of the 5' end of the gene because variations in the number of the T bases can result in frame shift mutations which cause premature termination of the encoded peptide thereby controlling expression of the U83A gene (FIG. 1) (Dewin et al., 2006; Tweedy et al., 2015b). This appears to be controlled by a herpesvirus DNA editing mechanism, which promotes variation in a number of human herpesvirus. For example, in herpes simplex virus, human alphaherpesvirus 1 and 2, DNA editing occurs at poly C or G tracts, which can occur in this GC rich genome, these give rise to homopolymer frame shift mutations (HFM), resulting due to individual variations in the homopolymer tracts; while in HHV-6, an AT rich genome, HFM occur here in a poly T tract (Dewin et al., 2006; Tweedy et al., 2015b; Tweedy et al., 2016; Tweedy et al., 2017). Only with an in frame set of poly T bases can the full gene be expressed which then encodes the N-terminal signal sequence required for co-translational insertion into the endoplasmic reticulum, followed by cleavage and processing for secretion of the mature U83A chemokine-like molecule. In the circulating virus, this is actually a rare variant, most have disrupted U83A genes via the poly T tract, and evidence has been presented that this can vary during a single infection (Dewin et al., 2006; Tweedy et al., 2015b). However, distinct from the virus, in the integrated genome of ciHHV-6A, ciU83A genomes integrated at the 17p locus at the subtelomere/telomere region, only have the poly T tract that permits the full length ciU83A molecule to be produced. Deep sequencing shows this is the dominant or only form, unlike in circulating virus (Tweedy et al., 2015a; Tweedy et al., 2015b; Tweedy et al., 2016; Tweedy et al., 2017). This form, iciU83A, has only two non-synonymous SNPs, giving coding changes compared to circulating virus U83A (FIG. 2). One of these are in the N-terminal regions, but are part of natural variation in the exogenous viruses (Clark et al., 2013). The second is the mutation proximal to the splice acceptor site (FIG. 2). Since the N-terminal region is maintained compared to the virus U83A, this shows sharing of receptor specificities. Only the C-terminal signaling domain has this single non-synonymous mutation.

Analyses of the length of the poly T tract in strain variants and other integrated virus genomes, shows that the full length gene can only be stabilized if the poly T tract is disrupted. Therefore, to fix the gene in the full-length encoded functional version, this poly T tract is mutated here, while retaining the same codon usage and coding potential. This discovery fixes this gene in the functional version, encoding as signal sequence so the mature product can be secreted (FIG. 1) and is introduced here for function for iciU83A and ciU83A-N (SEQ ID NO 2, 6 and 8; FIG. 7).

The U83A and ciU83A further share two other novel features in their gene structures, which affect gene expression. First, both contain a direct repeat TACC, which is novel to this gene. Further, the TACC motif forms part of a non-consensus splice donor and acceptor pair CT-AC, which we previously identified in the disrupted smaller gene product (French et al., 1999). The splice donor/acceptor pair in the circulating virus gene U83A, is however recognised by the cellular splicing apparatus, most likely via the minor spliceosome, since it is spliced when individually expressed in human cell lines (French et al., 1999; Lin et al., 2010). Although both these features are present in the iciU83A gene, the predicted splicing effects are completely different. The U83A gene characteristically is spliced to introduce a stop codon at the splice site, resulting in a truncated U83A-N product half the size of the full length product. However, this stop codon, TGA, is mutated in the ciU83A-N, to TGG (FIGS. 1 and 2) (while in frame with the full length iciU83A gene this give rise to the coding mutation Asp-Gly; FIG. 2) and since this is proximal to the splice acceptor site could also disrupt splicing. Indeed, as described above, this spliced form has not been disclosed or published in the prior art.

Figure 5:
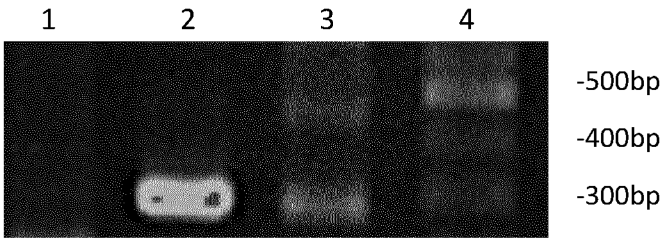
FIG. 5 shows in vitro expression in cells of iciU83A-N cDNA. The cDNA of iciU83A-N was cloned into a plasmid expression construct and transfected into HEK293 cells. Two days after transfection total RNA was extracted. The RNA was DNAse treated, lanes 2 and 3, then reverse transcriptase treated, lane 2, or untreated, lane 3. Negative control in lane 1 is water template only. Lane 4 shows the DNA markers.

Using plasmid DNA expression vectors, containing a human cytomegalovirus IE gene promoter and SV40 virus polyadenylation site, we cloned this product and transduced into cell lines, HEK293, using transfection reagent. RNA was extracted then analysed by reverse transcription polymerase chain reaction, RT-PCR. The results showed that this splice donor site is utilised, and moreover that the spliced product, now reads through the site of the previous stop codon, and unusually extends the coding region by eight amino acids as described above (FIGS. 4 and 5). Importantly, this feature can be used in diagnostics using suitable oligonucleotide primers to determine expression of the integrated form (FIG. 3).

In the circulating virus, the encoded full length U83A is rare, due to control by both the poly T tract disrupting the gene, as well as the non-consensus cellular splicing, truncating the full length product. Late in infection the splicing can be suppressed, resulting in read through of the full-length gene product (Dewin et al., 2006; Tweedy et al., 2015b). In order to simulate this effect in the absence of controls exerted by the circulating virus gene expression, both the direct repeat and the splice donor/acceptor pair can be mutated. This has been done on the iciU83A gene while maintaining both codon usage and coding potential as shown herein. In SEQ ID Nos 6 to 8, we have modified full-length iciU83A to stabilize expression for the uses described herein. SEQ ID NO: 6: Removes N-terminal heterogeneity; SEQ ID NO: 7: Prevents splicing; SEQ ID NO: 8 Removes N-terminal heterogeneity and prevents splicing. Therefore, these products are now uniquely fixed, to remove heterogeneity, SEQ ID No. 6 and 8, or to fix the full length version, SEQ ID NO: 7 and 8, for utility for immunostimulation as reviewed (Pontejo et al., 2018) and as below.

As described above, the integrated iciHHV-6A genome retains the AT compositional bias distinct from that of the human host. Increased protein expression has been demonstrated for other virus genes when the biased composition is matched to that of the human host. To do this, we followed the latest compilations and predictive programs changing the codon usage to match that of the human genome for both U83A and iciU83A as well as U83A-N and iciU83A-N cDNAs (including utilizing public databases as HIVE db). These were then further modified to adjust the poly T tract as well as any remaining of the TACC motif and the non-consensus donor/acceptor sites. These gene constructs can be used where optimum expressed protein concentration is required for example, for the uses described herein (FIG. 7), SEQ ID NO 9 (SEQ ID NO: 9 shows iciU83A mutated to prevent N-terminal heterogeneity, disrupt the TACC direct repeats and remove the splice donor/acceptor sites to fix the gene expression in a stable full-length agonist form with maximized human codon usage (including using HIVE db)

Example 2

In Vivo Expression in a Preclinical Model Shows Protection in Vaccine Utility In order to evaluate efficacy of the novel virokine derived from iciU83A-N, termed here VTL1, it was trialled in a preclinical model of infectious disease to evaluate its ability as an immunotherapeutic. This was first in a prophylactic DNA vaccine formulation, proprietary, in an HSV2 model system of sexually transmitted disease, STD. HSV2 infects approximately 400 million people worldwide with major disease recurrent STD, genital herpes, the most serious forms require continual therapy with toxic drugs and also significantly promotes HIV transmission, and causes neonatal disease with high mortality, 60% fatality (Looker et al., 2017; Looker et al., 2015; Looker et al., 2020). Therefore, an HSV2 vaccine is required to prevent infection or disease, yet despite many trials an effective vaccine has not been produced. A prophylactic vaccine could eliminate transmission and new disease, particularly required for discordant partners and those affected by HIV. The VTL1 virokine could promote immune cell recruitment to enhance vaccination as well as inhibit HIV by binding to the CCR5 co-receptor as it retains the ligand binding moiety as described above.

There are well established preclinical small animal models to evaluate treatment or prevention of HSV2 disease. The recommended preclinical model from the regulatory perspective is the Guinea pig model, as this correlates with human disease, and demonstrates the recurrences of infection as in the human disease. This model resembles more the human disease as it appears the only small animal model permitting evaluation of spontaneous recurrences (Strasser et al., 2000). Further neutralising antibodies levels and protection from disease appear linked to human disease protection. The current gold standard is this model system which has been used as a positive control to compare experimental vaccines, is the protein formulation of a secreted section of the gD glycoprotein, gD306 to amino acid residue 306 after cleavage of the signal sequence as used in clinical trials. This is formulated with the combined adjuvant, MPL and alum, which represents the adjuvant formulated with this protein in a recent clinical trial (Belshe et al., 2012). This trial showed a correlate of protection with neutralising antibodies, but interestingly only to HSV1 but not to HSV2 (Belshe et al., 2014). This indicated that raising this response could increase the protection in people.

A complication of using protein is that the amount needs to purified and standardised, as well as its stability and toxicity evaluated. DNA vaccines are superior in the increased safety, and ability to scale effectively with low production costs. A drawback is their inability to stimulate sufficient protective immunity in the clinic. However, these have been successful in aquaculture. Therefore, with sufficient immunological boost in an antigen formulation this should be possible. Previously, using murine model systems, the human chemokine CCL5 has been demonstrated to boost immunological responses to the gD encoded DNA (Sin et al., 2000). In this efficacy analyses, a DNA platform approach is used to compare immunological boost with that of the chemokine like VTL1 virokine in the guinea pig model. We use an antigen formulation containing the DNA encoding the known immunogen gD. This is compared to negative control of no prior vaccination and the gold standard positive control of the protein vaccine, which as described above has had the most success in clinical trials to date, gD306 formulated with MPL and alum.

The study design followed standard protocols established previously (Strasser et al., 2000). This follows the Guinea pig model with two to three immunisations injected intramuscularly separated by three weeks then challenged by virus delivered intravaginally. In the study, VTL1 is evaluated with a gD DNA formulation in a prophylactic vaccine study in the guinea pig preclinical model of HSV2 infection. Here, in order to maximally test the effect of this product tested, a sub optimal regime of 2 rather than 3 vaccine doses, was used in comparison to previous tests using gD plasmid (Bernstein et al., 1999; Strasser et al., 2000), this was combined with a higher virus challenge titer. The chemokine VTL1 DNA, iciU83A-N mutated for stable expression as in SEQ ID NO: 2, was synthesized and constructed in an expression plasmid containing a promoter for gene expression from human cytomegalovirus 1E1 gene with transcription termination signals by the SV40 polyadenylation and termination signal. In addition to the coding sequence each construct retained the native Kozak consensus sequence. The sequences were confirmed in the constructs as shown (SEQ ID NO:2) with the adjacent plasmid sequences determined giving in frame expression. The DNA constructs encoding VTL1 (mutated iciU83A-N, SEQ ID NO:2) were formulated with 0.25% bupivacaine as described (Bernstein et al., 1999). These were compared to negative control, no immunisation, and positive control the gold standard gD subunit protein vaccine formulated with MPL/Alum. For the two DNA vaccines, 300 micrograms of total DNA were used which comprised for VTL2gD (containing known immunogen HSV2 gD), followed by VTL2gD+VTL1 DNA formulation comprising 200 micrograms VTL2gD formulation with 100 micrograms of VTL1 DNA. The VTL1 DNA (iciU83A-N mutated variant, SEQ ID NO: 2) encoded VTL1 46 amino acids, SEQ ID NO. 4). All vaccines were delivered by the intramuscular, IM, route. There were 12 animals in each group.

Two doses were administered in a volume of 0.1 ml IM three weeks apart. Viral challenge ($1\times10^6$ pfu, HSV-2 strain MS) was given intravaginally three weeks after the last immunisation. The virus was inoculated into the vaginal vault as described (Bernstein et al., 1999). The animals were examined daily for acute disease to day 14 (FIG. 6). All animals in the negative control group showed the vesicular lesions characteristic of acute disease. In contrast the positive control group, gD subunit protein plus MPL/Alum adjuvant, showed only 25% (3/12) with disease. In the VTL test samples these showed near complete protection similar levels to the positive control of 25% (3/12) with disease, VTL2gD+VTL1. These levels of protection were significantly effective compared to the negative control (p<0.01).

As shown in FIG. 6 the total lesions experienced were significantly reduced or eliminated in the VTL immunised animals compared to the negative control. Those without immunisation had a mean total lesion score (days 4-14 post-inoculation) for severity of 8.29 (SD6.57) compared to the positive control subunit protein vaccine of 0.67 (SD 1.48), and the VTL vaccines of the immunogen formulation VTL2gD+ the VTL1 immunomodulator of 0.33 (SD 0.62). These results were better than the subunit protein positive control and showed highly significant, almost complete protection compared to the negative control (p<0.0001). These were also markedly improved over previous experimentation using full length HSV2gD2 plasmid expressed on its own using a similar protocol which showed total lesions score of 2.7 (+/−0.7) compared to the negative control in that experiment of 5.9 (+/−0.5) (Strasser et al 2000). In summary the VTL DNA vaccines containing human VTL1 integrated virus encoded chemokine like molecule, virokine, showed efficient protection as DNA vaccines exceeding that of the adjuvanted subunit protein vaccine previously used in clinical trials.

Example 3

In Vivo Expression in a Preclinical Model Shows Vaccine Utility in Preventing Disease and Reducing Virus Infection In order to further evaluate the efficacy of the novel virokine derived from iciU83A-N termed here VTL1 or in the figures VIT1 for Virokine Immune Therapeutic, further assays were conducted to evaluate its utility in preventing acute disease and virus infection. The assays performed included total scoring for disease severity as demonstrated in EXAMPLE 2 together with follow up for plaque titration of vaginal swabs to determine effects on virus infection post virus challenge after the immunisation protocol described in EXAMPLE 2. The efficacy endpoints were incidence and severity of acute disease plus the effect on virus vaginal replication as measured by virus titration by plaque assay.

Statistics were performed for all in vivo examples using Graphpad Prism with one-way ANOVA using Dunnett's test for multiple comparisons for the different vaccine treatments vs no vaccine. Where non-Gaussian distributions, non-parametric comparisons using Wilcoxon test were used. Significance was noted at P values<0.05 (*), <0.01 (), <0.001 (*).

The groups in the in vivo preclinical model study were:

1. No vaccine=negative control No Vaccine
2. VTL2gD DNA+VIT1=VTL2gD DNA+VIT1 DNA (i.e. VIT1 vaccine)
3. VTL2gD DNA=VTL2gD DNA in experiments shown
4. gD protein+mpl/alum=positive control previously clinically trialled gD306 (secreted)+adjuvant MPL/Alum VTL2gD DNA is a formulation containing DNA encoding a known immunogen glycoprotein gD of HSV2. DNA formulations contained 0.25% bupivacaine as described (Bernstein et al., 1999) The positive control, gD protein with an adjuvant formulation similar to MPL/alum have already shown some activity in protecting from HSV1 infection in human clinical trials and were similar to activity in preclinical trials using the guinea pig model system (Belshe et al 2012; Bourne et al., 2003) thus can be used to show a clinically relevant response in the guinea pig model. While this particular positive control is used in the following experiments to show clinical utility, it would be clear to the skilled person that any other composition that is also similarly capable of inducing an immune response to the virus in question would also be suitable.

VIT1, which is also known as VTL1, is the DNA described in this application of virus chemokine-like gene human adapted—virokine immune therapeutic (splice variant, SEQ ID NO: 2).

3.1 Incidence and Severity of Acute Disease

The DNA VIT1 formulations (including SEQ ID NO: 2) are tested in comparisons to negative control-no vaccine- or positive control-gD protein (secreted gD306)+MPL/alum adjuvant-similar to the formulation used in earlier clinical trials showing partial protection to HSV2 and HSV1 in women (Belshe et al, 2012).

The VTL2gD+VIT1 shows effective protection exceeding that shown for the positive control of gD protein MPL/alum.

This is also shown by analyses of the total acute, primary disease, mean lesion score shown for the individual animals in each test cohort (12 animals, 11 animals in the no vaccine group). The VIT1 vaccine treated individuals have significantly lowered scores.

Daily mean lesion scores can be seen in FIG. 6, where total mean scores per individual are significantly reduced, as well as the animals affected, as can be seen in FIG. 7, with the VIT1 vaccine showing almost complete protection.

3.2. Effect on Virus Vaginal Replication

The results on the effect of the treatment on lesion development are compared to effects on virus shedding during the primary disease. Analyses of the significantly lowered vaginal virus load correlates with the disease protection shown with close to log reduction of virus shed as for the gD protein formulation, using the suboptimal 2 dose immunisations.

By 8 days post virus challenge the VIT1 vaccine formulation has significantly reduced virus shedding to undetectable levels in almost all animals, $p<0.01$ (FIGS. 8A and 8B).

Example 4

In Vivo Expression in a Preclinical Model Shows Vaccine Utility in Preventing Detectable Latent Infection and as Therapeutic for Preventing Recurrent Persistent Infectious Disease Here the VIT1 (SEQ ID NO: 2) containing vaccine is evaluated for utility in preventing virus reactivation, recurrent disease and latent, persistent infection. The in vivo preclinical model described in EXAMPLE 2 has extended follow-up to 63 days post-challenge with virus, HSV2, after the two immunisations schedule with the vaccines. The assays performed include DNA PCR of vaginal shedding swabs and DNA PCR of the sites for latent infection, the dorsal root ganglion, DRG, and spinal cord. The efficacy endpoints were the effects on recurrent disease, asymptomatic shedding and latent viral burden. The limit on detection were marked and measured for virus quantification at 0.7 log pfu/ml and for qPCR undetectable below the limit of detection at 0.5 log microgm copies DNA/ml.

4.1. Effect on Recurrent Disease

The effects of the vaccine treatments on virus reactivation and recurrences of disease were analysed 15 to 63 days post infection challenge. Cumulative daily lesions were plotted and total mean lesion scores per individual compared.

This showed that the VTL2gD DNA vaccine with VIT1 could only prevent recurrent disease in combination with VIT1, demonstrating VIT1 utility as a therapeutic.

Distinctly, addition of the VIT1 chemokine DNA to the VTL2gD DNA treatment, gave effective control of recurrent lesions. This was similar to the positive control gD protein subunit vaccine formulation, $p<0.05$ and $p<0.01$ respectively, indicating clinical utility (FIGS. 9 and 10).

Both the VTL2gD DNA+VIT1 and gD protein subunit vaccine formulation halved lesion days in those with disease while most of the animals were completely protected from any disease recurrences (7/12 58%).

4.2. Effect on Virus Reactivation Shown by Asymptomatic Shedding

The effects of the vaccine treatments were tested for reductions on virus shedding after evidence for virus reactivation after day 20 post virus challenge. To do this the DNA load assayed in vaginal swabs by quantitative PCR was used as a surrogate for virus secretion.

Analyses of reactivated virus in recurrent shedding events and the total mean load in vaccinated compared to unvaccinated animals were carried out. While the gD protein subunit vaccine had no effect, there was a trend for reduced virus shedding for the VTL2gD DNA+VIT formulation, and the animals who received the VIT1 vaccine had almost half the overall load ($p=0.1$) and a third shedding events (20% reduced to 14 recurrences) (FIGS. 11 and 12).

4.3. Effect on Latent Viral Burden

The effects on establishment of latent infections at sites in the dorsal root ganglia and the spinal cord were assayed. At the end of the study, day 63 post virus challenge, the DNA present was quantified using qPCR at these sites of latency. Similar to the trend on virus secretion, analyses of the total mean DRG loads showed all vaccines significantly reduced levels compared to no vaccine, with the VTL2gD DNA+VIT1 vaccine halving amounts, $p<0.01$ (FIG. 13). Over half of the animals treated with VTL2gD DNA+VIT1 were protected from detectable DNA in the DRG, compared to <20% of the animals who received no vaccine (FIG. 14).

Analyses of latent DNA detected in the spinal cord showed similar effects with both positive control protein subunit and VIT1 vaccines significantly reducing the latent DNA load in the spinal cord ($p<0.05$). However, only the VTL2gD DNA+VIT1 vaccine significantly reduced numbers of animals with detection of DNA in the spinal cord, which was not seen with the gD subunit protein vaccine (FIGS. 15 and 16).

4.4. Summary

The VTL2gD DNA+VIT formulations were highly effective against acute, primary disease and virus replication. The VIT1 vaccine had an effect on reactivated virus infections reducing recurrent virus shedding, not seen with the protein subunit vaccine positive control, which had some efficacy in clinical trials, but required greater activity. Also with VIT1 there were reductions in both on primary and recurrent disease, not seen without VIT1, as well as significant reductions in the detection of latent burden, with over half animals completely protected. Only one animal died in the study and only in the no vaccine group, with two further animals in this group with severe infections preventing sample collection. In comparison, the VIT1 vaccine was safe, showed infection and disease protection with no adverse effects (summarised in Table 1).

TABLE 1

| Protection | Negative control - No vaccine | Positive control - gD protein | VTL2gD DNA + VIT1 |
|---|---|---|---|
| Prevent acute, primary disease | − | + | ++ |
| Reduce acute, | − | + | ++ |

TABLE 1-continued

| Protection | Negative control - No vaccine | Positive control - gD protein | VTL2gD DNA + VIT1 |
|---|---|---|---|
| primary vaginal virus replication | | | Undetectable by d8 |
| Reduce recurrent virus disease | − | + | + (Positive plus VIT, Negative minus VIT) |
| Reduce reactivated virus asymptomatic shedding | − | − | + trend (Positive plus VIT, Negative minus VIT) |
| Reduce latent viral burden | − | ++ | ++ |

This was a suboptimal dosing schedule for this model system (2 immunisations instead of 3) and improvement may be found in increased dosing or other routes of delivery. VIT1 (encoded by SEQ ID NOs: 1, 2, 3) can also be presented in the opposite modality for stimulation as an on/off switch (SEQ ID NOs: 7, 8, 9) and pending active splicing SEQ ID NO: 6 could encode both products for combined utility.

The cellular recruitment offered by the VIT virokines show enhanced effects on virus reactivation and recurrences. Cellular immunity is known to affect control of virus reactivation and recurrences. This also demonstrates that VIT can act as an immune therapeutic.

VIT1 is human adapted so effects in human settings are likely to further improve outcomes. Comparison in an ex vivo assay showed a related molecule with 100× greater efficacy than CCL5 in an HIV infection protection assay, consistent with CCR5 activities (Catusse et al 2007). Therefore, the protective effects in the human system are likely to be higher for VIT1, and combined with earlier data defining higher affinity for interactions with human chemokine receptors (Dewin et al 2006), warrants further investigation in a clinical setting as a preventative and therapeutic vaccine treatment for HSV2 and related HSV1, and further demonstrates utility as an immunomodulatory treatment in new types of vaccine formulations to provide efficient protection from disease or infection.

SEQUENCE LISTING

```
SEQ ID NO: 1: The VTL101 ciU83A-N nucleotide sequence cDNA
GTCGAAATGTCCATTCGGCTTTTTATTGGTTTTTTTTATACGGCATATATTGGTATGGCTATCG
GATTTATATGTAGTTCCCCCGATGCGGAGCTGTTTTCCGAAAAATCACGTATTTCGTCTTCTGT
CTTGTTAGGATGTTTGTTGTGTTGCATGGATTGGTCCGCTGCCGTACCCGTCTGGTTTGGAGCA
GGGCTCGATGTGTGA

SEQ ID NO: 2 The VTL1016 ciU83A-N nucleotide sequence cDNA, mutated
in the poly T tract (underlined) with own Kozak sequence.
GTCGAAATGTCCATTCGGCTTTTTATTGGTTTCTTTTATACGGCATATATTGGTATGGCTATCG
GATTTATATGTAGTTCCCCCGATGCGGAGCTGTTTTCCGAAAAATCACGTATTTCGTCTTCTGT
CTTGTTAGGATGTTTGTTGTGTTGCATGGATTGGTCCGCTGCCGTACCCGTCTGGTTTGGAGCA
GGGCTCGATGTGTGA

SEQ ID NO: 3 The VTL1017 ciU83A cDNA human codon optimised and
manually adjusted with no poly T and no TACC
GTCGAAATGTCCATCCGCCTTTTCATTGGCTTCTTTTACACAGCATACATCGGGATGGCTATAG
GCTTCATTTGCTCCTCTCCAGACGCGGAGCTGTTTTCAGAGAAAAGCCGGATATCTAGTAGCGT
GCTGCTCGGATGTCTGCTCTGTTGCATGGACTGGTCCGCTGCCGTCCCAGTGTGGTTCGGCGCT
GGACTGGATGTGTGA

SEQ ID NO: 4 The ciU83A-N cDNA encoded amino acid sequence-from VTL101,
VTL1016 and VTL1017 showing the additional C-terminal extension of 8
amino acids (underlined).
MSIRLFIGFFYTAYIGMAIGFICSSPDAELFSEKSRISSSVLLGCLLCCMDWSAAVPVWFGAGL
DV

SEQ ID NO: 5 The ciU83A-N cDNA encoded amino acid sequence cleaved
after signal sequence to give mature secreted product
(again C-terminal extension 8 amino acids-underlined)
from VTL101, VTL1016 and VTL1017.
FICSSPDAELFSEKSRISSSVLLGCLLCCMDWSAAVPVWFGAGLDV

SEQ ID NO: 6 The VTL1018 iciU83A DNA mutated to disrupt the poly T
region, underlined, and retaining own Kozak sequence.
GTCGAAATGTCCATTCGGCTTTTTATTGGTTTCTTTTATACGGCATATATTGGTATGGCTATCG
GATTTATATGTAGTTCCCCCGATGCGGAGCTGTTTTCCGAAAAATCACGTATTTCGTCTTCTGT
CTTGTTAGGATGTTTGTTGTGTTGCATGGATTGGTCCGCTGCCGTACCTGGGAAAACAGAGCCT
TTTAGAAAACTTTTTGATGCAATCATGATTAAAAAGCTAAAAAGTTGTTCTGCTGCTTACCCGT
CTGGTTTGGAGCAGGGCTCGATGTGTGATATGGCAGATGCATCGCCGACAAGTCTTGAATTAGG
ATTGTCGAAATTAGACAAAGAATCATGA

SEQ ID NO: 7 The VTL1019 iciU83A DNA mutated to disrupt the splicing
via the direct repeat TACC and the splice donor/acceptor sites, as
underlined and retaining Kozak consensus site.
GTCGAAATGTCCATTCGGCTTTTTATTGGTTTTTTTTATACGGCATATATTGGTATGGCTATCG
GATTTATATGTAGTTCCCCCGATGCGGAGCTGTTTTCCGAAAAATCACGTATTTCGTCTTCTGT
CTTGTTAGGATGTTTGTTGTGTTGCATGGATTGGTCCGCTGCCGTGCCAGGGAAAACAGAGCCT
TTTAGAAAACTTTTTGATGCAATCATGATTAAAAAGCTAAAAAGTTGTTCTGCTGCTTATCCAT
CTGGTTTGGAGCAGGGCTCGATGTGTGATATGGCAGATGCATCGCCGACAAGTCTTGAATTAGG
ATTGTCGAAATTAGACAAAGAATCATGA
```

-continued

SEQUENCE LISTING

```
SEQ ID NO: 8 The VTL1020 iciU83A DNA mutated to disrupt the poly T
region and the splicing, as underlined and retaining own Kozak sequence.
GTCGAAATGTCCATTCGGCTTTTTATTGGTTTCTTTTATACGGCATATATTGGTATGGCTATCG
GATTTATATGTAGTTCCCCCGATGCGGAGCTGTTTTCCGAAAAATCACGTATTTCGTCTTCTGT
CTTGTTAGGATGTTTGTTGTGTTGCATGGATTGGTCCGCTGCCGTGCCAGGGAAAACAGAGCCT
TTTAGAAAACTTTTTGATGCAATCATGATTAAAAAGCTAAAAAGTTGTTCTGCTGCTTATCCAT
CTGGTTTGGAGCAGGGCTCGATGTGTGATATGGCAGATGCATCGCCGACAAGTCTTGAATTAGG
ATTGTCGAAATTAGACAAAGAATCATGA

SEQ ID NO: 9 The VTL1021 iciU83A DNA maximized for human codon useage
and manually adjusted to disrupt the splicing, as underlined and retain
Kozak sequence.
GTCGAAATGAGCATCAGACTGTTCATCGGCTTCTTCTACACCGCCTACATCGGCATGGCCATCG
GCTTCATCTGCAGCAGCCCCGACGCCGAGCTGTTCAGCGAGAAGAGCAGAATCAGCAGCAGCGT
GCTGCTGGGCTGCCTGCTGTGCTGCATGGACTGGAGCGCCGCCGTGCCAGGCAAGACCGAGCCC
TTCAGAAAGCTGTTCGACGCCATCATGATCAAGAAGCTGAAGAGCTGCAGCGCCGCCTATCCTA
GCGGCCTGGAGCAGGGCAGCATGTGCGACATGGCCGACGCCAGCCCCACCAGCCTGGAGCTGGG
CCTGAGCAAGCTGGACAAGGAGAGCTGA

SEQ ID NO: 10 and 11: Diagnostic primers for the detection of
integrated iciU83A and iciU83A-N genes and transcripts, together
with diagnostic probes or primers SEQ ID NO: 12 and 13.

For whole gene:
5'ATGTCCATTCGGCTTTTTATTG 3' SEQ ID NO: 10

5'TCATGATTCTTTGTCTAATTTC3' SEQ ID NO: 11

SEQ ID NO: 12 and 13: Diagnostic probes, or primer retaining
diagnostic 3' nucleotide underlined for iciU83A, SEQ ID NO: 12,
and for iciU83A-N, SEQ ID NO: 13
5'AAAAAGCTAAAAAGTTGTTCTGCTGCTTACCCGTCTGG3' SEQ ID NO: 12

5'TGGTCCGCTGCCGTACCCGTCTGG3' SEQ ID NO: 13

SEQ ID NO: 14 Encoded amino acid sequence of VTL1018, VTL1019, VTL1020
and VTL1021
M S I R L F I G F F Y T A Y I G M A I G
F I C S S P D A E L F S E K S R I S S S
V L L G C L L C C M D W S A A V P G K T
E P F R K L F D A I M I K K L K S C S A
A Y P S G L E Q G S M C D M A D A S P T
S L E L G L S K L D K E S -

SEQ ID NO: 15: Signal sequence cleaved mature secreted encoded amino
acid sequence of VTL10118, VTL1019 and VTL1020
F I C S S P D A E L F S E K S R I S S S
V L L G C L L C C M D W S A A V P G K T
E P F R K L F D A I M I K K L K S C S A
A Y P S G L E Q G S M C D M A D A S P T
S L E L G L S K L D K E S -
```

REFERENCES

Bayry, J., Tchilian, E. Z., Davies, M. N., Forbes, E. K., Draper, S. J., Kaveri, S. V., Hill, A. V., Kazatchkine, M. D., Beverley, P. C., Flower, D. R., and Tough, D. F. (2008). In silico identified CCR4 antagonists target regulatory T cells and exert adjuvant activity in vaccination. Proc Natl Acad Sci USA 105, 10221-10226.

Belshe, R. B., Heineman, T. C., Bernstein, D. I., Bellamy, A. R., Ewell, M., van der Most, R., and Deal, C. D. (2014). Correlate of immune protection against HSV-1 genital disease in vaccinated women. J Infect Dis 209, 828-836.

Belshe, R. B., Leone, P. A., Bernstein, D. I., Wald, A., Levin, M. J., Stapleton, J. T., Gorfinkel, I., Morrow, R. L., Ewell, M. G., Stokes-Riner, A., et al. (2012). Efficacy results of a trial of a herpes simplex vaccine. N Engl J Med 366, 34-43.

Bernstein, D. I., Tepe, E. R., Mester, J. C., Arnold, R. L., Stanberry, L. R., and Higgins, T. (1999). Effects of DNA immunization formulated with bupivacaine in murine and guinea pig models of genital herpes simplex virus infection. Vaccine 17, 1964-1969.

Bobanga, I. D., Petrosiute, A., and Huang, A. Y. (2013). Chemokines as Cancer Vaccine Adjuvants. Vaccines (Basel) 1, 444-462.

Bourne, N., Bravo, F. J., Francotte, M., Bernstein, D. I., Myers, M. G., Slaoui, M., Stanberry, L. R. (2003). Herpes Simplex Virus (HSV) Type 2 Glycoprotein D subunit vaccines and protection against genital HSV-1 or HSV-2 disease in guinea pigs. J Infect Dis 187, 542-549.

Catusse, J., Clark, D. J., and Gompels, U. A. (2009). CCR5 signalling, but not DARC or D6 regulatory, chemokine receptors are targeted by herpesvirus U83A chemokine which delays receptor internalisation via diversion to a caveolin-linked pathway. J Inflamm (Lond) 6, 22.

Catusse, J., Parry, C. M., Dewin, D. R., and Gompels, U. A. (2007). Inhibition of HIV-1 infection by viral chemokine U83A via high-affinity CCR5 interactions that block human chemokine-induced leukocyte chemotaxis and receptor internalization. Blood 109, 3633-3639.

Clark, D. J., Catusse, J., Stacey, A., Borrow, P., and Gompels, U. A. (2013). Activation of CCR2+ human proinflammatory monocytes by human herpesvirus-6B chemokine N-terminal peptide. J Gen Virol 94, 1624-1635.

Dewin, D. R., Catusse, J., and Gompels, U. A. (2006). Identification and characterization of U83A viral chemokine, a broad and potent beta-chemokine agonist for human CCRs with unique selectivity and inhibition by spliced isoform. J Immunol 176, 544-556.

French, C., Menegazzi, P., Nicholson, L., Macaulay, H., DiLuca, D., and Gompels, U. A. (1999). Novel, nonconsensus cellular splicing regulates expression of a gene encoding a chemokine-like protein that shows high variation and is specific for human herpesvirus 6. Virology 262, 139-151.

Greninger, A. L., Knudsen, G. M., Roychoudhury, P., Hanson, D. J., Sedlak, R. H., Xie, H., Guan, J., Nguyen, T., Peddu, V., Boeckh, M., et al. (2018). Comparative genomic, transcriptomic, and proteomic reannotation of human herpesvirus 6. BMC Genomics 19, 204.

Kamei, N., Tamiwa, H., Miyata, M., Haruna, Y., Matsumura, K., Ogino, H., Hirano, S., Higashiyama, K., and Takeda-Morishita, M. (2018). Hydrophobic Amino Acid Tryptophan Shows Promise as a Potential Absorption Enhancer for Oral Delivery of Biopharmaceuticals. Pharmaceutics 10.

Konstantina, T., Konstantinos, R., Anastasios, K., Anastasia, M., Eleni, L., loannis, S., Sofia, A., and Dimitris, M. (2019). Fatal adverse events in two thymoma patients treated with anti-PD-1 immune check point inhibitor and literature review. Lung Cancer 135, 29-32.

Kwok, G., Yau, T. C., Chiu, J. W., Tse, E., and Kwong, Y. L. (2016). Pembrolizumab (Keytruda). Hum Vaccin Immunother 12, 2777-2789.

Lin, C. F., Mount, S. M., Jarmolowski, A., and Makalowski, W. (2010). Evolutionary dynamics of U12-type spliceosomal introns. BMC Evol Biol 10, 47.

Looker, K. J., Magaret, A. S., May, M. T., Turner, K. M. E., Vickerman, P., Newman, L. M., and Gottlieb, S. L. (2017). First estimates of the global and regional incidence of neonatal herpes infection. Lancet Glob Health 5, e300-e309.

Looker, K. J., Magaret, A. S., Turner, K. M., Vickerman, P., Gottlieb, S. L., and Newman, L. M. (2015). Global estimates of prevalent and incident herpes simplex virus type 2 infections in 2012. PLoS One 10, e114989.

Looker, K. J., Welton, N. J., Sabin, K. M., Dalal, S., Vickerman, P., Turner, K. M. E., Boily, M. C., and Gottlieb, S. L. (2020). Global and regional estimates of the contribution of herpes simplex virus type 2 infection to HIV incidence: a population attributable fraction analysis using published epidemiological data. Lancet Infect Dis 20, 240-249.

Peddu, V., Dubuc, I., Gravel, A., Xie, H., Huang, M. L., Tenenbaum, D., Jerome, K. R., Tardif, J. C., Dube, M. P., Flamand, L., and Greninger, A. L. (2019). Inherited Chromosomally Integrated Human Herpesvirus 6 Demonstrates Tissue-Specific RNA Expression In Vivo That Correlates with an Increased Antibody Immune Response. J Virol 94.

Pontejo, S. M., Murphy, P. M., and Pease, J. E. (2018). Chemokine Subversion by Human Herpesviruses. J Innate Immun 10, 465-478.

Sin, J., Kim, J. J., Pachuk, C., Satishchandran, C., and Weiner, D. B. (2000). DNA vaccines encoding interleukin-8 and RANTES enhance antigen-specific Th1-type CD4 (+) T-cell-mediated protective immunity against herpes simplex virus type 2 in vivo. J Virol 74, 11173-11180.

Singh, S., Datta, A., Schmidtchen, A., Bhunia, A., and Malmsten, M. (2017). Tryptophan end-tagging for promoted lipopolysaccharide interactions and anti-inflammatory effects. Sci Rep 7, 212.

Strasser, J. E., Arnold, R. L., Pachuk, C., Higgins, T. J., and Bernstein, D. I. (2000). Herpes simplex virus DNA vaccine efficacy: effect of glycoprotein D plasmid constructs. J Infect Dis 182, 1304-1310.

Tweedy, J., Spyrou, M. A., Donaldson, C. D., Depledge, D., Breuer, J., and Gompels, U. A. (2015a). Complete Genome Sequence of the Human Herpesvirus 6A Strain AJ from Africa Resembles Strain GS from North America. Genome Announc 3.

Tweedy, J., Spyrou, M. A., Hubacek, P., Kuhl, U., Lassner, D., and Gompels, U. A. (2015b). Analyses of germline, chromosomally integrated human herpesvirus 6A and B genomes indicate emergent infection and new inflammatory mediators. J Gen Virol 96, 370-389.

Tweedy, J., Spyrou, M. A., Pearson, M., Lassner, D., Kuhl, U., and Gompels, U. A. (2016). Complete Genome Sequence of Germline Chromosomally Integrated Human Herpesvirus 6A and Analyses Integration Sites Define a New Human Endogenous Virus with Potential to Reactivate as an Emerging Infection. Viruses 8.

Tweedy, J. G., Escriva, E., Topf, M., and Gompels, U. A. (2017). Analyses of Tissue Culture Adaptation of Human Herpesvirus-6A by Whole Genome Deep Sequencing Redefines the Reference Sequence and Identifies Virus Entry Complex Changes. Viruses 10.

Vilgelm, A. E., and Richmond, A. (2019). Chemokines Modulate Immune Surveillance in Tumorigenesis, Metastasis, and Response to Immunotherapy. Front Immunol 10, 333.

Yau, W. M., Wimley, W. C., Gawrisch, K., and White, S. H. (1998). The preference of tryptophan for membrane interfaces. Biochemistry 37, 14713-14718.

The invention claimed is:

1. An isolated polynucleotide comprising the nucleic acid sequence of any one of SEQ ID NOs: 1-3, 6-9, and a nucleic acid sequence complementary thereto.

2. The isolated polynucleotide of claim 1, comprising a nucleic acid sequence selected from the group consisting of: SEQ ID NO: 2, 3, 6, 7, 8 and 9.

3. A nucleic acid construct comprising the isolated polynucleotide of claim 1.

4. A host cell comprising the nucleic acid construct of claim 3.

5. An isolated polypeptide comprising the amino acid sequence of SEQ ID NO: 4, 5, 14, or 15.

6. A pharmaceutical composition comprising the isolated polynucleotide of claim 1, or an isolated polypeptide comprising the amino acid sequence of SEQ ID NO: 4, 5, 14, or 15 and a pharmaceutically acceptable carrier.

7. An adjuvant formulation comprising the isolated polynucleotide of claim 1, or an isolated polypeptide comprising the amino acid sequence of SEQ ID NO: 4, 5, 14, or 15.

8. A vaccine or therapeutic composition comprising the isolated polynucleotide of claim 1, or an isolated polypeptide comprising the amino acid sequence of SEQ ID NO: 4, 5, 14, or 15 or a polypeptide variant thereof having at least 90% overall sequence identity to one of SEQ ID NOs: 4, 5, 14, and 15.

9. A kit for treating a disorder characterised by altered levels of one or more of CCR1, CCR4, CCR5, CCR6 and CCR8, or their binding chemokines, the kit comprising the isolated polynucleotide of claim 1, or an isolated polypeptide comprising the amino acid sequence of SEQ ID NO: 4, 5, 14, 15, together with instructions for treating said disorder.

10. The isolated polynucleotide of claim 1, comprising the nucleic acid sequence of SEQ ID NO: 1 or the nucleic acid sequence complementary thereto.

11. The isolated polynucleotide of claim 1, comprising a nucleic acid sequence selected from the group consisting of: SEQ ID NO: 2, 3, 6, 7, 8 and 9.

12. A nucleic acid construct comprising the isolated polynucleotide of claim 10.

13. A host cell comprising the nucleic acid construct of claim 12.

14. A pharmaceutical composition comprising the isolated polynucleotide of claim 1 comprising the nucleic acid sequence of SEQ ID NO: 1 or the nucleic acid sequences complementary thereto, or an isolated polypeptide comprising the amino acid sequence of SEQ ID NO: 4, 5, 14, or 15; and a pharmaceutically acceptable carrier.

15. An adjuvant formulation comprising the polynucleotide of claim 1 comprising the nucleic acid sequence of SEQ ID NO: 1 or the nucleic acid sequence complementary thereto, or an isolated polypeptide comprising the amino acid sequence of SEQ ID NO: 4, 5, 14, or 15.

16. A vaccine or therapeutic composition comprising the isolated polynucleotide of claim 1 comprising the nucleic acid sequence of SEQ ID NO: 1 or the nucleic acid sequence complementary thereto, or an isolated polypeptide comprising the amino acid sequence of SEQ ID NO: 4, 5, 14, or 15; and a vaccine antigen.

17. A kit for treating a disorder characterised by altered levels of one or more of CCR1, CCR4, CCR5, CCR6 and CCR8, or their binding chemokines, the kit comprising the isolated polynucleotide of claim 1 comprising the nucleic acid sequence of SEQ ID NO: 1 or the nucleic acid sequence complementary thereto, or an isolated polypeptide comprising the amino acid sequence of SEQ ID NO: 4, 5, 14, or 15; together with instructions for treating said disorder.

18. The isolated polynucleotide of claim 1, wherein the isolated polynucleotide encodes a hydrophobic C-terminal amino acid sequence identical to the last 8 amino acid of SEQ ID: 4.

19. The isolated polypeptide of claim 5, comprising a hydrophobic C-terminal amino acid sequence identical to the last 8 amino acid of SEQ ID: 4.

* * * * *